United States Patent
Shachar et al.

(10) Patent No.: US 7,869,854 B2
(45) Date of Patent: Jan. 11, 2011

(54) APPARATUS FOR MAGNETICALLY DEPLOYABLE CATHETER WITH MOSFET SENSOR AND METHOD FOR MAPPING AND ABLATION

(75) Inventors: Yehoshua Shachar, Santa Monica, CA (US); Laszlo Farkas, Ojai, CA (US); Eli Gang, Beverly Hills, CA (US)

(73) Assignee: Magnetecs, Inc., Inglewood, CA (US)

( * ) Notice: Subject to any disclaimer, the term of this patent is extended or adjusted under 35 U.S.C. 154(b) by 1013 days.

(21) Appl. No.: 11/362,542

(22) Filed: Feb. 23, 2006

(65) Prior Publication Data

US 2007/0197891 A1 Aug. 23, 2007

(51) Int. Cl.
*A61B 5/04* (2006.01)
(52) U.S. Cl. .................................... 600/374
(58) Field of Classification Search ........... 606/34, 606/32; 600/393, 374, 508, 509
See application file for complete search history.

(56) References Cited

U.S. PATENT DOCUMENTS

| | | | |
|---|---|---|---|
| 3,043,309 A | 7/1962 | McCarthy |
| 3,358,676 A | 12/1967 | Frei et al. |
| 3,622,869 A | 11/1971 | Golay |
| 3,628,527 A | 12/1971 | West |
| 3,746,937 A | 7/1973 | Koike |
| 3,961,632 A | 6/1976 | Moossun |
| 4,063,561 A | 12/1977 | McKenna |
| 4,096,862 A | 6/1978 | DeLuca |
| 4,162,679 A | 7/1979 | Reenstierna |
| 4,173,228 A | 11/1979 | Van Steenwyk et al. |

(Continued)

FOREIGN PATENT DOCUMENTS

DE 102005045073 A1 3/2007

(Continued)

OTHER PUBLICATIONS

Faddis, Mitchell, et al. Novel, Magnetically Guided Catheter for Endocardial Mappaing and Radiofrequency Catheter Ablation. Journal of the American Heart Association. [retrieved online: Jun. 22, 2009]. Nov. 11, 2022.*

(Continued)

*Primary Examiner*—George Manuel
(74) *Attorney, Agent, or Firm*—Knobbe, Martens, Olson & Bear, LLP

(57) ABSTRACT

A mapping and ablation catheter is described. In one embodiment, the catheter includes a MOSFET sensor array that provides better fidelity of the signal measurements as well as data collection and reduces the error generated by spatial distribution of the isotropic and anisotropic wavefronts. In one embodiment, the system maps the change in potential in the vicinity of an activation wavefront. In one embodiment, the mapping system tracks the spread of excitation in the heart, with properties such as propagation velocity changes. In one embodiment, during measurement, the manifold carrying the sensor array expands from a closed position state to a deployable open state. Spatial variation of the electrical potential is captured by the system's ability to occupy the same three-dimensional coordinate set for repeated measurements of the desired site. In one embodiment, an interpolation algorithm tracks the electrogram data points to produce a map relative to the electrocardiogram data.

33 Claims, 26 Drawing Sheets

U.S. PATENT DOCUMENTS

| | | |
|---|---|---|
| 4,244,362 A | 1/1981 | Anderson |
| 4,249,536 A | 2/1981 | Vega |
| 4,270,252 A | 6/1981 | Harrison et al. |
| 4,292,961 A | 10/1981 | Kawashima |
| 4,354,501 A | 10/1982 | Colley et al. |
| 4,392,634 A | 7/1983 | Kita |
| 4,671,287 A | 6/1987 | Fiddian-Green |
| 4,727,344 A | 2/1988 | Koga et al. |
| 4,735,211 A | 4/1988 | Takasugi |
| 4,809,713 A | 3/1989 | Grayzel |
| 4,869,247 A | 9/1989 | Howard, III et al. |
| 4,943,770 A | 7/1990 | Ashley-Rollman et al. |
| 4,984,581 A | 1/1991 | Stice |
| 4,985,015 A | 1/1991 | Obermann et al. |
| 5,063,935 A | 11/1991 | Gambale |
| 5,083,562 A | 1/1992 | de Coriolis et al. |
| 5,090,956 A | 2/1992 | McCoy |
| 5,125,888 A | 6/1992 | Howard et al. |
| 5,167,626 A | 12/1992 | Casper et al. |
| 5,209,234 A | 5/1993 | LaRocca |
| 5,226,847 A | 7/1993 | Thomas et al. |
| 5,249,163 A | 9/1993 | Erickson |
| 5,255,680 A | 10/1993 | Darrow et al. |
| 5,257,636 A | 11/1993 | White |
| 5,269,759 A | 12/1993 | Hernandez et al. |
| 5,353,807 A | 10/1994 | DeMarco |
| 5,377,678 A | 1/1995 | Dumoulin et al. |
| 5,396,902 A | 3/1995 | Brennen et al. |
| 5,492,131 A | 2/1996 | Galel |
| 5,546,948 A | 8/1996 | Hamm et al. |
| 5,550,469 A | 8/1996 | Tanabe et al. |
| 5,558,091 A | 9/1996 | Acker et al. |
| 5,573,012 A | 11/1996 | McEwan |
| 5,588,442 A | 12/1996 | Scovil et al. |
| 5,624,430 A | 4/1997 | Eton et al. |
| 5,645,065 A | 7/1997 | Shapiro et al. |
| 5,650,725 A | 7/1997 | Powell et al. |
| 5,654,864 A | 8/1997 | Ritter et al. |
| 5,656,030 A | 8/1997 | Hunjan et al. |
| 5,681,260 A | 10/1997 | Ueda et al. |
| 5,683,384 A * | 11/1997 | Gough et al. .................. 606/41 |
| 5,702,433 A | 12/1997 | Taylor et al. |
| 5,704,897 A | 1/1998 | Truppe |
| 5,709,661 A | 1/1998 | Van Egmond et al. |
| 5,711,299 A | 1/1998 | Manwaring et al. |
| 5,769,843 A | 6/1998 | Abela et al. |
| 5,775,322 A | 7/1998 | Silverstein et al. |
| 5,779,694 A | 7/1998 | Howard et al. |
| 5,808,665 A | 9/1998 | Green |
| 5,821,920 A | 10/1998 | Rosenberg et al. |
| 5,843,153 A | 12/1998 | Johnston et al. |
| 5,844,140 A | 12/1998 | Seale |
| 5,904,691 A | 5/1999 | Barnett et al. |
| 5,931,818 A | 8/1999 | Werp et al. |
| 5,971,976 A | 10/1999 | Wang et al. |
| 6,014,580 A | 1/2000 | Blume et al. |
| 6,015,414 A | 1/2000 | Werp et al. |
| 6,038,488 A | 3/2000 | Barnes et al. |
| 6,104,944 A | 8/2000 | Martinelli |
| 6,122,538 A | 9/2000 | Sliwa et al. |
| 6,128,174 A | 10/2000 | Ritter et al. |
| 6,129,668 A | 10/2000 | Haynor et al. |
| 6,148,823 A * | 11/2000 | Hastings ..................... 128/897 |
| 6,152,933 A | 11/2000 | Werp et al. |
| 6,157,853 A | 12/2000 | Blume et al. |
| 6,200,312 B1 * | 3/2001 | Zikorus et al. ................ 606/32 |
| 6,241,671 B1 | 6/2001 | Ritter et al. |
| 6,292,678 B1 | 9/2001 | Hall et al. |
| 6,295,466 B1 * | 9/2001 | Ishikawa et al. ............ 600/509 |
| 6,296,604 B1 | 10/2001 | Garibaldi et al. |
| 6,304,768 B1 | 10/2001 | Blume et al. |
| 6,311,082 B1 | 10/2001 | Creighton, IV et al. |
| 6,314,312 B1 | 11/2001 | Wessels et al. |
| 6,315,709 B1 | 11/2001 | Garibaldi et al. |
| 6,330,467 B1 | 12/2001 | Creighton, IV et al. |
| 6,352,363 B1 | 3/2002 | Munger et al. |
| 6,364,823 B1 | 4/2002 | Garibaldi et al. |
| 6,375,606 B1 | 4/2002 | Garibaldi et al. |
| 6,381,485 B1 | 4/2002 | Hunter et al. |
| 6,385,472 B1 | 5/2002 | Hall et al. |
| 6,401,723 B1 | 6/2002 | Garibaldi et al. |
| 6,428,551 B1 | 8/2002 | Hall et al. |
| 6,454,776 B1 | 9/2002 | Tajima et al. |
| 6,459,924 B1 | 10/2002 | Creighton, IV et al. |
| 6,459,926 B1 | 10/2002 | Nowlin et al. |
| 6,475,223 B1 | 11/2002 | Werp et al. |
| 6,505,062 B1 | 1/2003 | Ritter et al. |
| 6,507,751 B2 | 1/2003 | Blume et al. |
| 6,522,909 B1 | 2/2003 | Garibaldi et al. |
| 6,524,303 B1 | 2/2003 | Garibaldi |
| 6,529,761 B2 | 3/2003 | Creighton, IV et al. |
| 6,537,196 B1 | 3/2003 | Creighton, IV et al. |
| 6,562,019 B1 | 5/2003 | Sell |
| 6,575,977 B1 | 6/2003 | Michelson |
| 6,587,709 B2 | 7/2003 | Solf et al. |
| 6,594,517 B1 | 7/2003 | Nevo |
| 6,630,879 B1 | 10/2003 | Creighton, IV et al. |
| 6,662,034 B2 | 12/2003 | Segner et al. |
| 6,667,660 B2 * | 12/2003 | Schrodinger et al. ........ 330/289 |
| 6,669,693 B2 * | 12/2003 | Friedman .................... 606/41 |
| 6,677,752 B1 | 1/2004 | Creighton, IV et al. |
| 6,702,804 B1 | 3/2004 | Ritter et al. |
| 6,704,694 B1 | 3/2004 | Basdogan et al. |
| 6,726,675 B1 | 4/2004 | Beyar |
| 6,733,511 B2 | 5/2004 | Hall et al. |
| 6,740,103 B2 | 5/2004 | Hall et al. |
| 6,755,816 B2 | 6/2004 | Ritter et al. |
| 6,776,165 B2 | 8/2004 | Jin |
| 6,786,219 B2 | 9/2004 | Garibaldi et al. |
| 6,817,364 B2 | 11/2004 | Garibaldi et al. |
| 6,834,201 B2 | 12/2004 | Gillies et al. |
| 6,853,965 B2 | 2/2005 | Massie et al. |
| 6,902,528 B1 | 6/2005 | Garibaldi et al. |
| 6,914,552 B1 | 7/2005 | McEwan |
| 6,960,847 B2 | 11/2005 | Suzuki et al. |
| 7,280,863 B2 | 10/2007 | Shachar |
| 7,316,700 B2 * | 1/2008 | Alden et al. ................ 606/181 |
| 7,341,063 B2 | 3/2008 | Garibaldi et al. |
| 7,346,379 B2 | 3/2008 | Eng et al. |
| 7,495,537 B2 | 2/2009 | Tunay |
| 7,543,239 B2 | 6/2009 | Viswanathan et al. |
| 2001/0004215 A1 | 6/2001 | Kubota et al. |
| 2001/0021805 A1 | 9/2001 | Blume et al. |
| 2002/0022777 A1 | 2/2002 | Creighton, IV et al. |
| 2002/0055674 A1 | 5/2002 | Ben-haim et al. |
| 2002/0058866 A1 | 5/2002 | Segner et al. |
| 2002/0103430 A1 | 8/2002 | Hastings et al. |
| 2003/0205941 A1 | 11/2003 | Suzuki et al. |
| 2003/0233112 A1 * | 12/2003 | Alden et al. ................ 606/181 |
| 2004/0019447 A1 * | 1/2004 | Shachar .................... 702/115 |
| 2005/0004449 A1 | 1/2005 | Mitschke et al. |
| 2005/0096589 A1 | 5/2005 | Shachar |
| 2005/0256521 A1 | 11/2005 | Kozel |
| 2006/0114088 A1 | 6/2006 | Shachar |
| 2006/0116633 A1 | 6/2006 | Shachar |
| 2006/0116634 A1 | 6/2006 | Shachar |
| 2006/0217697 A1 | 9/2006 | Lau et al. |
| 2007/0016006 A1 | 1/2007 | Shachar |
| 2007/0062547 A1 | 3/2007 | Pappone |
| 2007/0197891 A1 | 8/2007 | Shachar |
| 2008/0027313 A1 | 1/2008 | Shachar |
| 2008/0249395 A1 | 10/2008 | Shachar et al. |
| 2008/0297287 A1 | 12/2008 | Shachar et al. |
| 2009/0248014 A1 | 10/2009 | Shachar et al. |

| | | | |
|---|---|---|---|
| 2009/0253985 | A1 | 10/2009 | Shachar et al. |
| 2009/0275828 | A1 | 11/2009 | Shachar et al. |

FOREIGN PATENT DOCUMENTS

| | | | |
|---|---|---|---|
| EP | 0147082 A2 | 7/1985 | |
| EP | 1 059 067 | 12/2000 | |
| EP | 1 115 327 | 7/2001 | |
| GB | 2367803 A | 4/2002 | |
| JP | 2000-509316 | 7/2000 | |
| JP | 2001-448 | 1/2001 | |
| JP | 2001-509038 | 7/2001 | |
| JP | 2001-514040 | 9/2001 | |
| WO | WO 95-01757 A1 | 1/1995 | |
| WO | WO 97-29803 A1 | 8/1997 | |
| WO | WO 98-35720 A2 | 8/1998 | |
| WO | WO 99-11189 A1 | 3/1999 | |
| WO | WO 99-23934 A2 | 5/1999 | |
| WO | WO 00-07641 A | 2/2000 | |
| WO | WO 02-19908 A | 3/2002 | |
| WO | WO 02-34131 A1 | 5/2002 | |
| WO | WO 02-094115 A2 | 11/2002 | |
| WO | WO 02-094115 A3 | 11/2002 | |
| WO | WO 2004-006795 A1 | 1/2004 | |
| WO | WO 2005-042053 A2 | 5/2005 | |
| WO | WO 2005-042053 A3 | 5/2005 | |
| WO | WO 2005-112813 A1 | 12/2005 | |
| WO | WO 2007-100559 A2 | 9/2007 | |

OTHER PUBLICATIONS

Office Action dated Feb. 5, 2008 from Related U.S. Appl. No. 10/621,196.
Office Action dated Dec. 2, 2008 from Related U.S. Appl. No. 10/621,196.
Office Action dated Jan. 29, 2009 from Related U.S. Appl. No. 11/331,781.
Office Action dated Feb. 25, 2009 from Related U.S. Appl. No. 11/331,944.
Office Action dated Apr. 28, 2009 From Related U.S. Appl. No. 11/331,485.
Office Action dated Feb. 22, 2006 from Related U.S. Appl. No. 10/621,196.
Office Action dated Nov. 14, 2006 from Related U.S. Appl. No. 10/621,196.
Office Action dated Apr. 18, 2007 from Related U.S. Appl. No. 10/621,196.
Office Action dated May 18, 2006 from Related U.S. Appl. No. 10/690,472.
Office Action dated Jan. 30, 2007 from Related U.S. Appl. No. 10/690,472.
Notice of Allowance dated Aug. 6, 2007 from Related U.S. Appl. No. 10/690,472.
International Search Report from PCT/US2007/004416, Aug. 24, 2007, 5 pages.
Bergveld, Piet, "Development, Operation, and Application of the Ion-Sensitive Field-Effect Transistor as a Tool for Electrophysiology", IEEE Transactions on Biomedical Engineering, vol. BME-19, No. 5, Sep. 1972, 10 pages.
Office Action dated Jul. 10, 2008 from Related U.S. Appl. No. 10/621,196.
Office Action dated Jun. 18, 2008 from Related U.S. Appl. No. 11/331,485.
Office Action dated Aug. 8, 2008 from Related U.S. Appl. No. 11/140,475.
International Search Report from PCT/US2008/060525, Oct. 31, 2008, 6 pages.
Office Action dated Sep. 10, 2007 from Related U.S. Appl. No. 10/621,196.
Advisory Action dated Nov. 6, 2007 from Related U.S. Appl. No. 10/621,196.
Fink et al.,"An Optically Switched PS-Radar for Pictorial Representation of Object Structures in Human Tissue," Experimentelle Technik Der Physik, vol. 38, No. 3, 1990, pp. 197-206, 10 pages.
International Search Report from PCT/US2008/056277, Nov. 18, 2008, 5 pages.
Supplementary Partial Search Report from 04795885.5, Nov. 18, 2008, 5 pages.
Extended European Search Report from 09005296.0, Aug. 19, 2009, 3 pages.
Faddis et al., "Novel, Magnetically Guided Catheter for Endocardial Mapping and Radiofrequency Catheter Ablation," Journal of the American Heart Association, Nov. 11, 2002.
International Search Report from PCT/US2009/039659, Sep. 3, 2009, 4 pages.
International Search Report from PCT Application No. PCT/US03/22122; 9 pages.
Office Action dated Aug. 25, 2009 from Related U.S. Appl. No. 10/621,196.
Advisory Action dated Mar. 6, 2007 from Related U.S. Appl. No. 10/621,196.
Office Action dated Dec. 22, 2005 from Related U.S. Appl. No. 10/621,196.
Office Action dated Jan. 30, 2007 from Related U.S. Appl. No. 10/690,472.
Office Action dated May 18, 2006 from Related U.S. Appl. No. 10/690,472.
Advisory Action dated Nov. 27, 2009 from Related U.S. Appl. No. 11/140,475.
Office Action dated Nov. 30, 2009 from Related U.S. Appl. No. 11/331,944.
Office Action dated Sep. 2, 2009 from Related U.S. Appl. No. 11/140,475.
Office Action dated Sep. 22, 2009 from Related U.S. Appl. No. 11/331,781.
Supplemental Notice of Allowance dated Aug. 6, 2007 from Related U.S. Appl. No. 10/690,472.
International Search Report from PCT/US2009/039659, Jul. 6, 2009, 4 pages.
Office Action dated Jul. 15, 2009 From Related U.S. Appl. No. 11/331,485.
Ishiyama, K.; Sendoh, M.; Arai, K.I.; Magnetic micromachines for medical applications. Journal of Magnetism and Magnetic Materials. 2002; vol. 242; pp. 41-46.
Ritter, J.A.; Ebner, A.D.;Daniel, K.D.; Stewart, K.L.; Application of high gradient magnetic separation principles to magnetic drug targeting. Journal of Magnetism and Magnetic Materials. 2004; vol. 280; pp. 184-201.
Totsu, K.; Haga, Y.; Esashi, M.; Three-axis magneto-impedance effect sensor system for detecting position and orientation of catheter tip. Sensors and Actuators. 2004; Issue A 111; pp. 304-309.

* cited by examiner

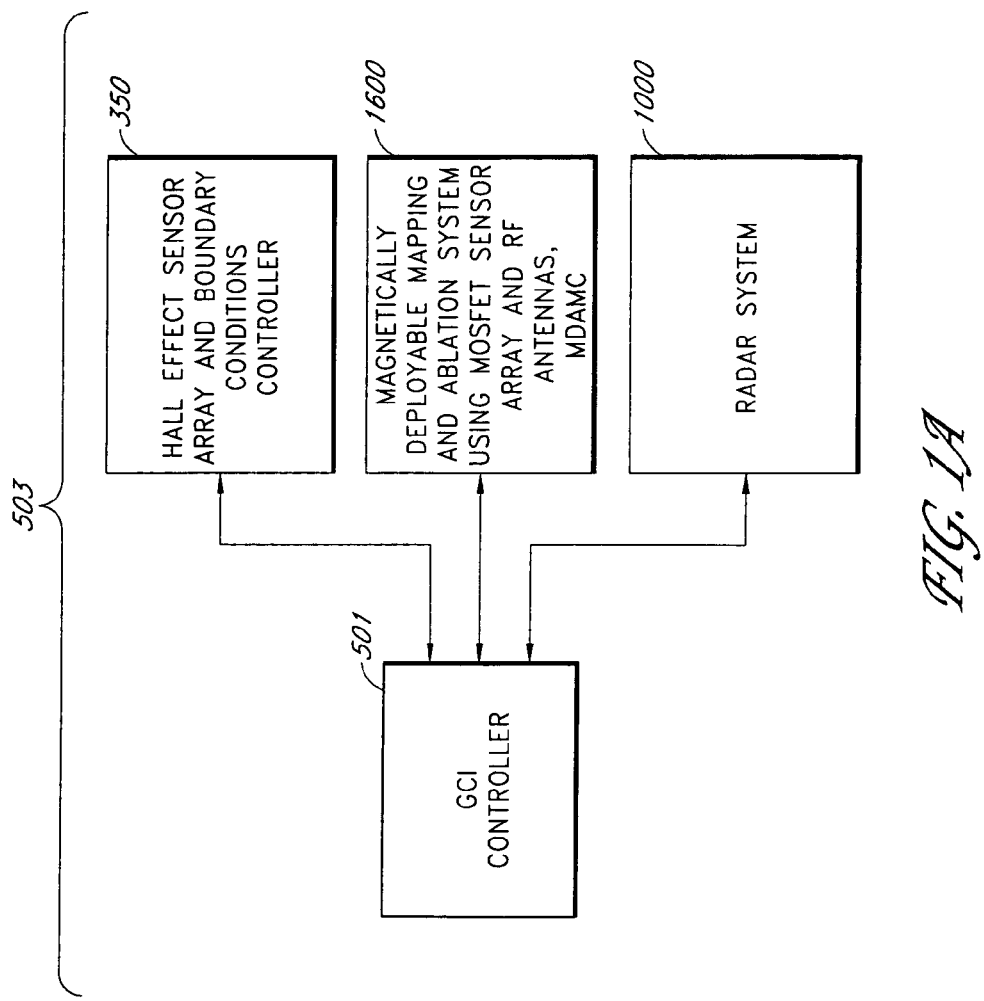

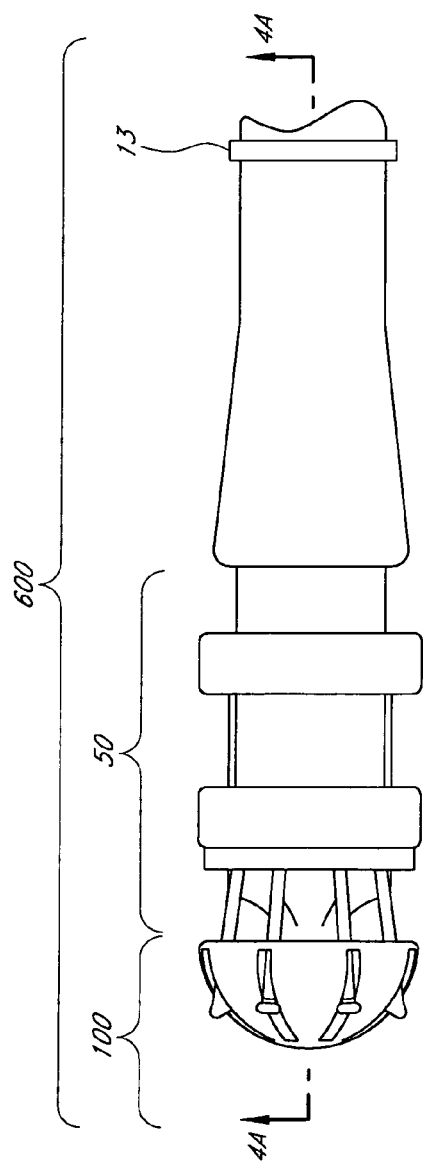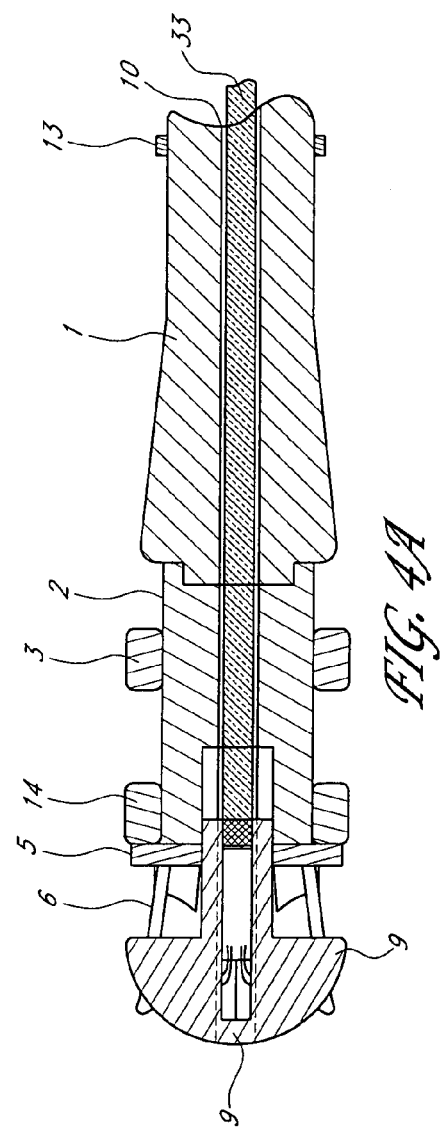
FIG. 4
FIG. 4A

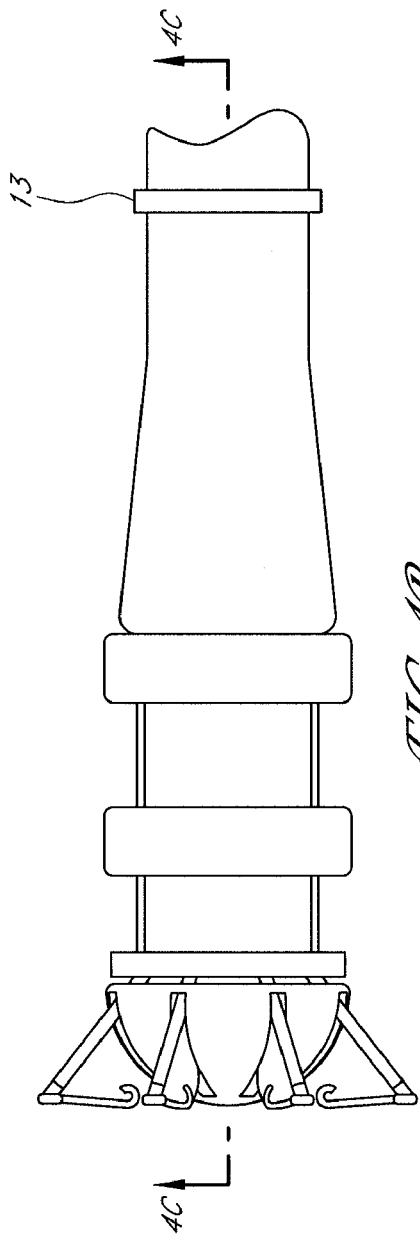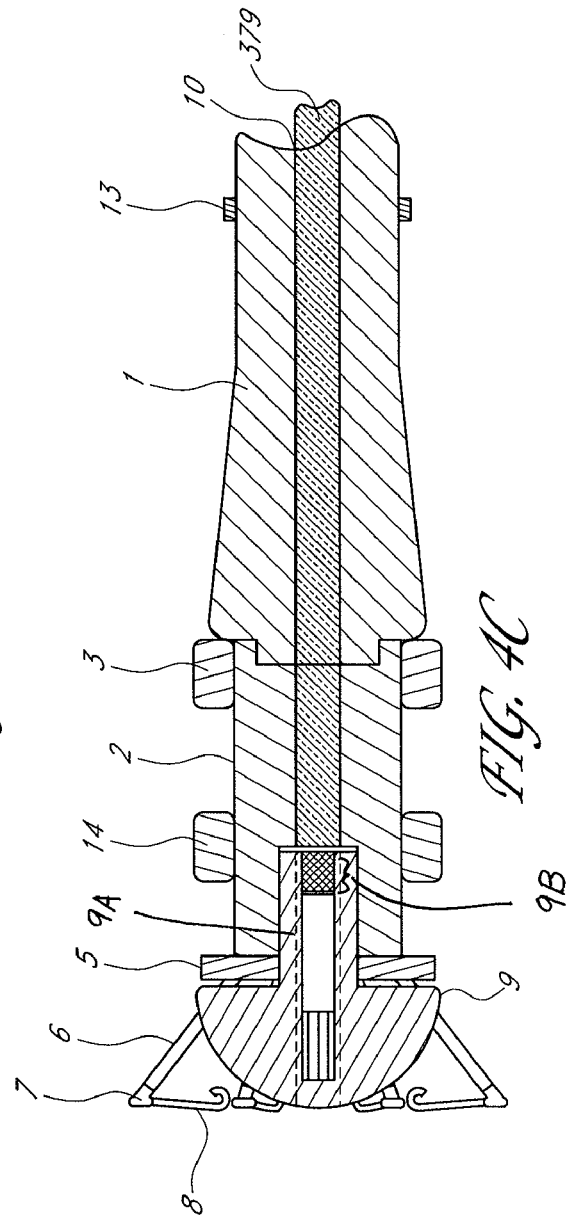

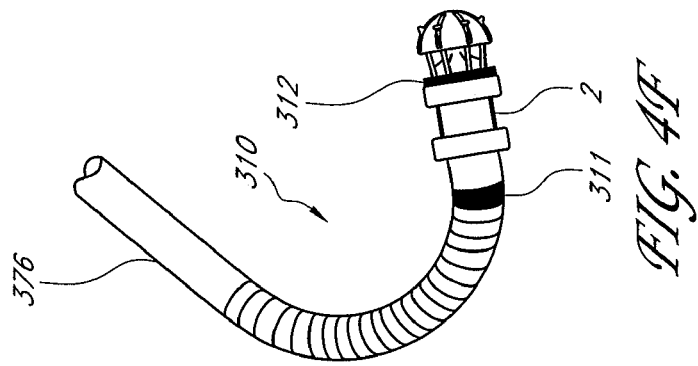
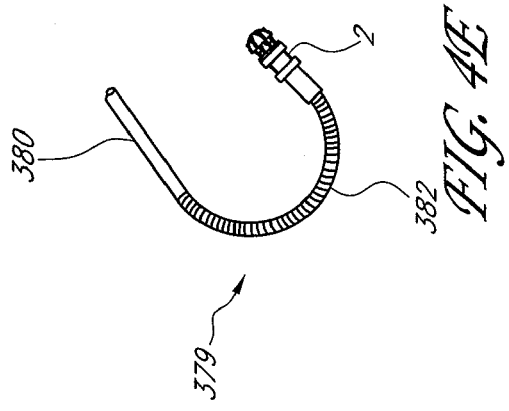
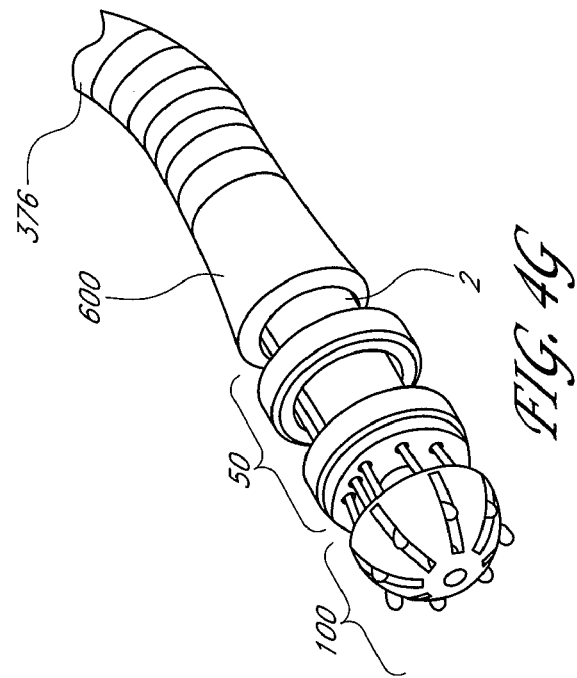
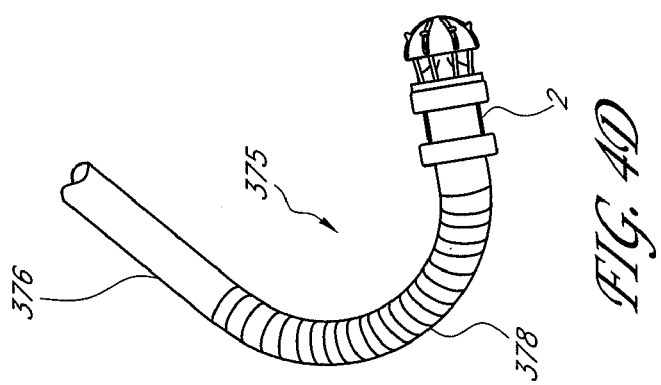

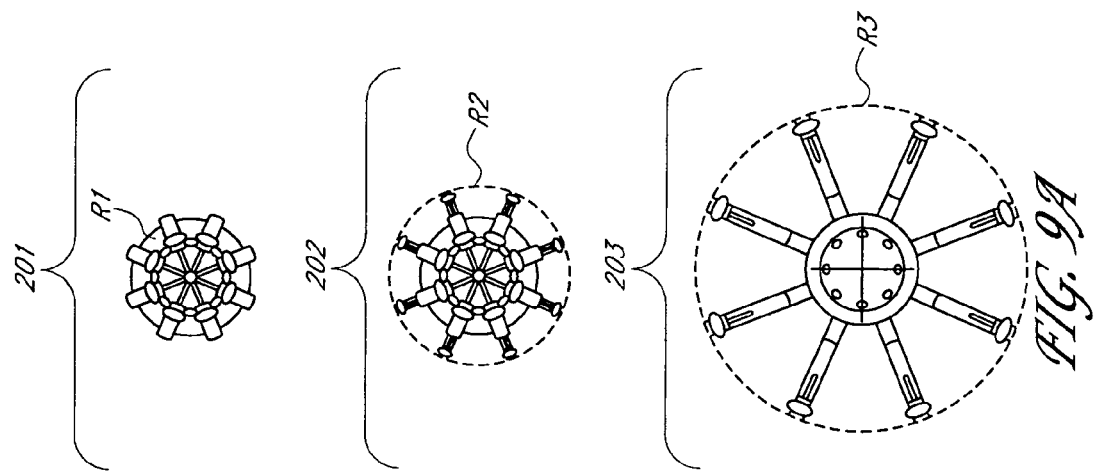
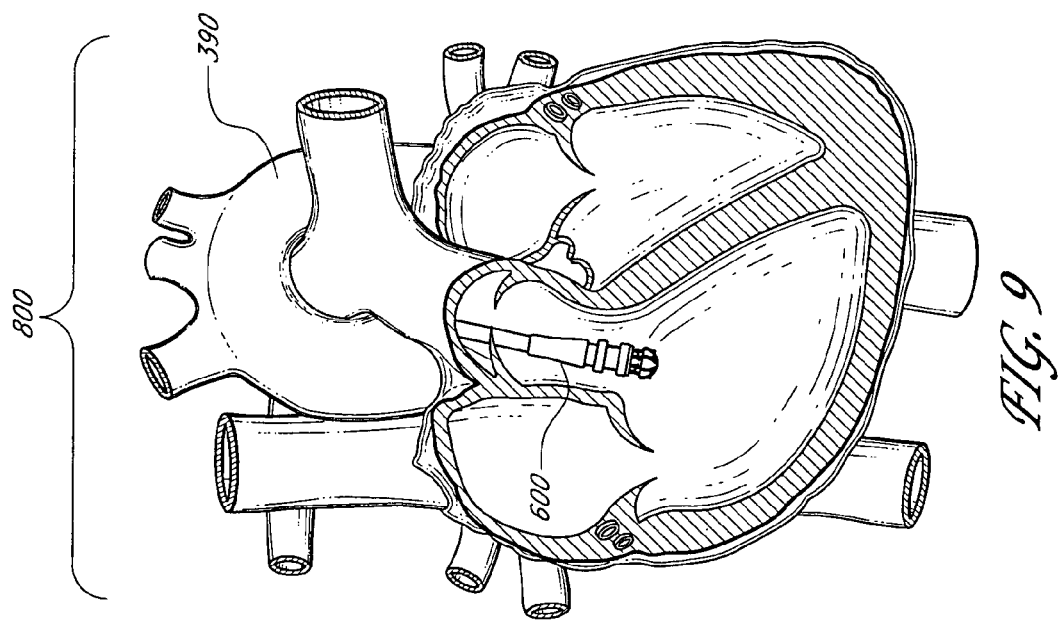

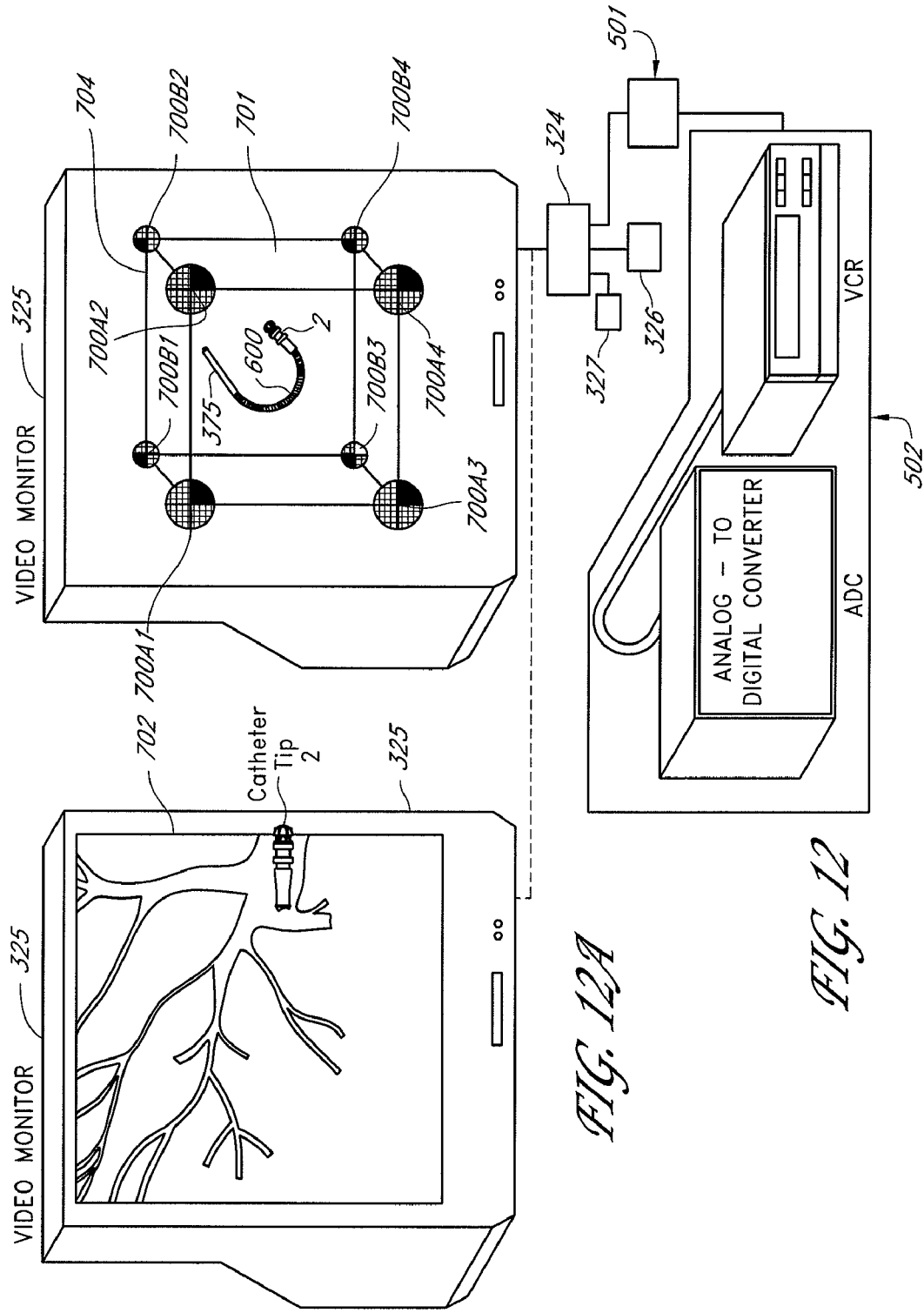

APPARATUS FOR MAGNETICALLY DEPLOYABLE CATHETER WITH MOSFET SENSOR AND METHOD FOR MAPPING AND ABLATION

FIELD OF THE INVENTION

A method and apparatus for navigating and recording electrical characteristics of the heart using a MOSFET sensor guided by a magnetically-deployable mechanism is described.

BACKGROUND

Cardiac mapping using catheters introduced percutaineously into the heart chambers while recording the electrical potential and subsequently correlating the endocardial electrograms to specific anatomy of the heart suffers from multiple drawbacks. The use of fluoroscopy for correlating geometry and metrics is limited by the two-dimensional imagery of the fluoroscopy. The geometrical interpolation of the data and error reduction technique used in order to "best fit" the electrode and the site is at best an approximation. Another drawback of the existing art is the inability of existing methods to determine the measurement position in order to collect additional data points.

Therefore, there is a substantial and unsatisfied need for an apparatus and method for guiding, steering, advancing, and locating the position of the mapping electrode for measurement of electrical potential and for providing a three-dimensional image data.

SUMMARY

These and other problems are solved by providing a magnetically-deployable catheter control and system using a MOSFET sensor array. In one embodiment, the sensor provides better fidelity of the signal measurements as well as data collection and reduces the error generated by spatial distribution of the isotropic and anisotropic wavefronts. In one embodiment, the system maps the change in potential in the vicinity of the activation wavefront, which provides data on the thickness of the activation wavefront. In one embodiment, the mapping system tracks the spread of excitation in the heart, with properties such as propagation velocity changes. In one embodiment, during measurement, the manifold carrying the sensor array expands from a closed position state to a deployable open state [umbrella], which can sample and hold a set of data points for each QRS cycle. Spatial variation of the electrical potential is captured by the system's ability to occupy the same three-dimensional coordinate set for repeated measurements of the desired site. In one embodiment, an interpolation algorithm tracks the electrogram data points so as to produce a map relative to the electrocardiogram data.

In one embodiment, a magnetically-deployable catheter uses a MOSFET sensor matrix for mapping and ablation. In one embodiment, a MOSFET sensor array and RF radiating antennas are configured to provide multiple states of deployable sensor configurations (radial). In one embodiment, radial umbrella-like arrays are used. The arrays sense activation spread as an energetic event. The dynamic variations of electric potential during de-polarization and re-polarization of the excitable cells of the heart can be measured as the activation avalanches.

In one embodiment, the electrical and magnetic fields during cell activation, are measured. In one embodiment, an algorithm describes these fields and calculates the dynamic spread of the energy contained in the electric and magnetic fields, and in the multi-source excitable cell of the hearts myocardium region.

The energy event as a methodology of representing the cardiac activation spread can be used for diagnostic and pathological assessment as well as for forming maps of the superimposed electric and energy wave upon the anatomical detail generated by x-ray imagery or other imaging methods (e.g., MRI, CAT scans, etc.).

In one embodiment, a magnetically-deployable catheter with MOSFET sensor controlled by a magnetic catheter guidance, control, and imaging apparatus as described in U.S. patent application Ser. No. 10/690,472 titled, "System and Method for Radar Assisted catheter Guidance and Control" and US Patent 2004/0019447 and provisional application No. 60/396,302, the entire contents of which are hereby incorporated by reference.

In one embodiment, the system provides ablation and mapping while navigating and controlling the movements of the sensors and antennas manually.

In one embodiment, the system provides electrocardiographic maps of the myocardium region.

In one embodiment, the ablation and mapping apparatus is magnetically-deployable using mechanism which provides the measurement of surface potential and activation time matrix by the use of a plurality of sensing points. This measurement is further refined (Error Reduction Technique) along one or more measurement radii change in desired increments, and further enhanced by measurement steps along the circumference for each radius.

The electric potential data table provides for at least 24 element pairs ($E_n$ and $t_n$) for each catheter position along the myocardium.

In one embodiment, the sensor head measures the conductivity matrix between the sensing points during activation. The measurement can be refined (Error Reduction Technique) along radii changed in desired increments. In one embodiment, the measurements fidelity is improved by rotating the measurements as a sequence of measurements around the circumference for each radius. The conductivity data table has multiple elements for each new catheter position along the myocardium.

In one embodiment, the mapping capabilities of electric potential and conductivity activation spread measurements is supplemented with a display of the magnitude and direction of the activation energy wave along the myocardium. This energy wave contains complimentary information to the electric field measurements about the anisotropy of the myocardium related to its conductivity during the activation excitation spread.

In one embodiment, the apparatus displays the directional anisotropy between the electric field and the conductivity vector for cardiac disorder or pathology correlation.

In one embodiment, the system includes an RF ablation tool. The RF ablation antennas can be selected and activated independently by configuring the driving RF (300 kHz to 1 MHZ) voltage phase-angle to obtain the required lesion geometry, such as, for example, elongated linear cuts with desired ablation depth.

In one embodiment, the ablation and mapping catheter uses the radar imaging and fiduciary marker technique identified by U.S. application Ser. No. 10/690,472, hereby incorporated by reference, for use by catheter fitted with magnetically coupled devices.

In one embodiment, the collected potential, timing, conductivity and energy wave data is interpolated between the sensors and extrapolated into the muscle tissues of the heart. The results are then overlaid and displayed together with the apparatus noted by application Ser. No. 10/690,472 or other imaging systems.

In one embodiment, the catheter guidance system includes a closed-loop servo feedback system. In one embodiment, a radar system is used to determine the location of the distal end of the catheter inside the body, thus, minimizing or eliminating the use of ionizing radiation such as X-rays. The catheter guidance system can also be used in combination with an X-ray system (or other imaging systems) to provide additional imagery to the operator. The magnetic system used in the magnetic catheter guidance system can also be used to locate the catheter tip to provide location feedback to the operator and the control system. In one embodiment, a magnetic field source is used to create a magnetic field of sufficient strength and orientation to move a magnetically-responsive catheter tip in a desired direction by a desired amount.

In one embodiment, a multi-coil cluster is configured to move and/or shape the location of a magnetic field in 3D space relative to the patient. This magnetic shape control function provides efficient field shaping to produce desired magnetic fields for catheter manipulations in the operating region (effective space).

One embodiment includes a catheter and a guidance and control apparatus that allows the surgeon/operator to position the catheter tip inside a patient's body. The catheter guidance and control apparatus can maintain the catheter tip in the correct position.

One embodiment includes a catheter and a guidance and control apparatus that can steer the distal end of the catheter through arteries and forcefully advance it through plaque or other obstructions.

One embodiment includes a catheter guidance and control apparatus that is more intuitive and simpler to use, that displays the catheter tip location in three dimensions, that applies force at the catheter tip to pull, push, turn, or hold the tip as desired, and that is configured to producing a vibratory or pulsating motion of the tip with adjustable frequency and amplitude to aid in advancing the tip through plaque or other obstructions. One embodiment provides tactile feedback at the operator control to indicate an obstruction encountered by the tip.

In one embodiment, the Catheter Guidance Control and Imaging (CGCI) system allows a surgeon to advance, position a catheter, and to view the catheter's position in three dimensions by using a radar system to locate the distal end of the catheter. In one embodiment, the radar data can be combined with X-ray or other imagery to produce a composite display that includes radar and image data. In one embodiment, the radar system includes a Synthetic Aperture Radar (SAR). In one embodiment, the radar system includes a wideband radar. In one embodiment, the radar system includes an impulse radar.

One embodiment includes a user input device called a "virtual tip." The virtual tip includes a physical assembly, similar to a joystick, which is manipulated by the surgeon/operator and delivers tactile feedback to the surgeon in the appropriate axis or axes if the actual tip encounters an obstacle. The Virtual tip includes a joystick type device that allows the surgeon to guide the actual catheter tip through the patient's body. When the actual catheter tip encounters an obstacle, the virtual tip provides tactile force feedback to the surgeon to indicate the presence of the obstacle. In one embodiment, the joystick includes a PHANTOM® Desktop™ haptic device manufactured by Sensable Technologies, Inc. In one embodiment, the virtual tip includes rotary control systems such as those manufactured by Hitachi Medical Systems America, Inc.

In one embodiment, the physical catheter tip (the distal end of the catheter) includes a permanent magnet that responds to the magnetic field generated externally to the patient's body. The external magnetic field pulls, pushes, turns, and holds the tip in the desired position. One of ordinary skill in the art will recognize that the permanent magnet can be replaced or augmented by an electromagnet.

In one embodiment, the physical catheter tip (the distal end of the catheter) includes a permanent magnet and two or more piezoelectric rings, or semiconductor polymer rings to allow the radar system to detect the second harmonics of the resonating signal emanating from the rings.

In one embodiment, the CGCI apparatus provides synchronization by using a radar and one or more fiduciary markers to provide a stereotactic frame of reference.

In one embodiment, the CGCI apparatus uses numerical transformations to compute currents to be provided to various electromagnets and position of one or more of the electromagnet to control the magnetic field used to push/pull and rotate the catheter tip in an efficient manner.

In one embodiment, the CGCI apparatus includes a motorized and/or hydraulic mechanism to allow the electromagnet poles to be moved to a position and orientation that reduces the power requirements desired to push, pull, and rotate the catheter tip.

In one embodiment, the CGCI apparatus is used to perform an implantation of a pacemaker during an electrophysiological (EP) procedure.

In one embodiment, the CGCI apparatus uses radar or other sensors to measure, report and identify the location of a moving organ within the body (e.g., the heart, lungs, etc.) with respect to the catheter tip and one or more fiduciary markers, so as to provide guidance, control, and imaging to compensate for movement of the organ, thereby, simplifying the surgeon's task of manipulating the catheter through the body.

In one embodiment, a servo system has a correction input that compensates for the dynamic position of a body part, or organ, such as the heart, thereby, offsetting the response such that the actual tip moves substantially in unison with the dynamic position (e.g., with the beating heart).

In one embodiment of the catheter guidance system: i) the operator adjusts the physical position of the virtual tip, ii) a change in the virtual tip position is encoded and provided along with data from a radar system, iii) the control system generates servo system commands that are sent to a servo system control apparatus, iv) the servo system control apparatus operates the servo mechanisms to adjust the position of one or more electromagnet clusters by varying the distance and/or angle of the electromagnet clusters and energizing the electromagnets to control the magnetic catheter tip within the patient's body, v) the new position of the actual catheter tip is then sensed by the radar, thereby, allowing synchronization and superimposing of the catheter position on an image produced by fluoroscopy and/or other imaging modality, vi) providing feedback to the servo system control apparatus and to the operator interface, and vii) updating the displayed image of the catheter tip position in relation to the patient's internal body structures.

BRIEF DESCRIPTION OF THE FIGURES

FIG. 1A is a block diagram of the imaging module for use in the CGCI surgery procedure that includes the catheter guidance system, a radar system, Hall Effect sensors and the mapping and ablation apparatus.

FIGS. 4, 4A, 4B and 4C shows an orthographic representation of the mapping and ablation catheter with its physical attributes.

FIGS. 4D, 4E, 4F, and 4G are orthographic depictions of a magnetically-deployable guidewire and ablation tool and catheter.

FIGS. 4I, 4J, 4K, 4L, and 4M are orthographic depictions of the wiring and electrical connections of the antennas, MOSFETs, and coils forming the circuit layout of the ablation and mapping assembly.

FIGS. 9 and 9A show the catheter with closed, intermediary and fully open geometry states.

FIGS. 12 and 12A show the manifold with its fiduciary markers used in forming the stereotactic frame.

DETAILED DESCRIPTION

Figure 1:
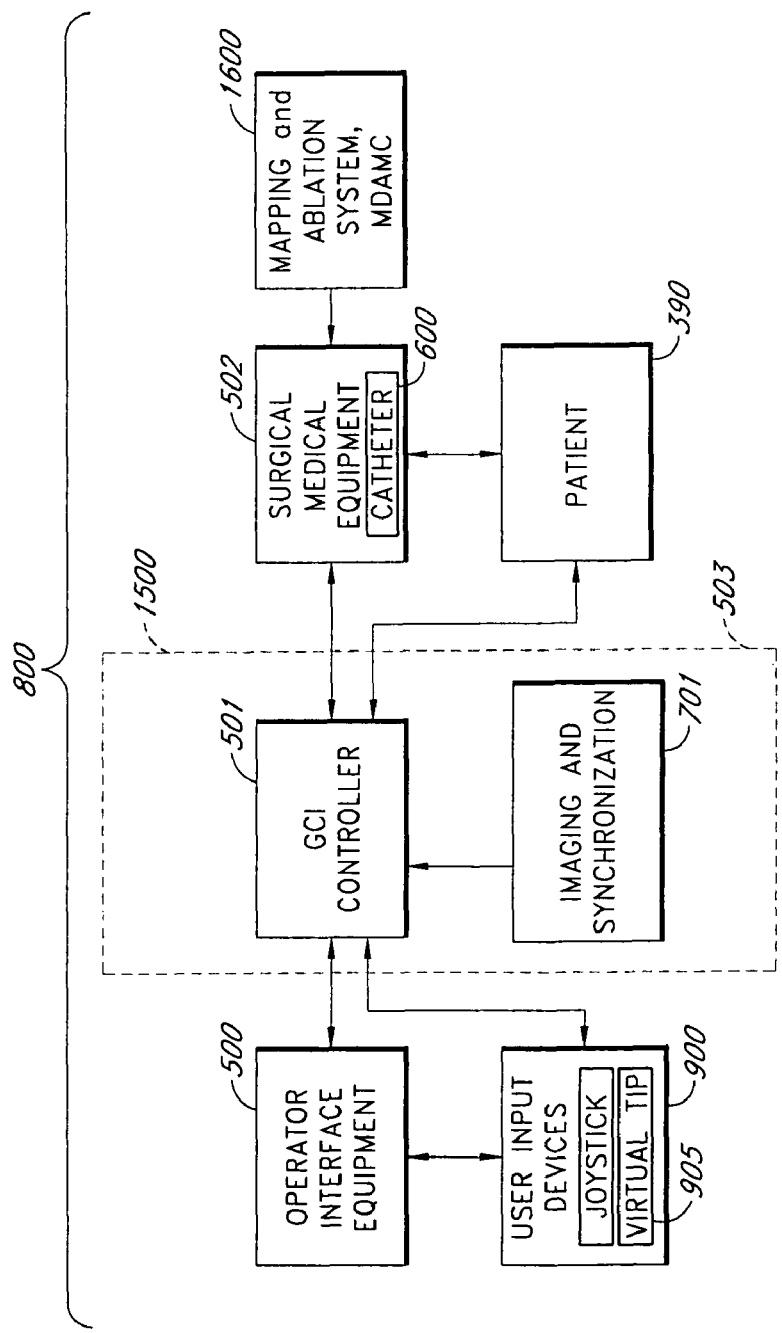
FIG. 1 is a system block diagram for a surgery system that includes an operator interface, a catheter guidance system (CGCI) and surgical equipment including a system for mapping and ablation apparatus.

FIG. 1 is a system block diagram for a surgery system 800 that includes an operator interface 500, a CGCI system 1500, the surgical equipment 502 (e.g., a catheter tip 2, etc.), one or more user input devices 900, and a patient 390. The user input devices 900 can include one or more of a joystick, a mouse, a keyboard, a virtual tip 905, and other devices to allow the surgeon to provide command inputs to control the motion and orientation of the catheter tip 2.

In one embodiment, the CGCI system 800 includes a controller 501 and an imaging synchronization module 701. FIG. 1 shows the overall relationship between the various functional units and the operator interface 500, auxiliary equipment 502, and the patient 390. In one embodiment, the CGCI system controller 501 calculates the Actual Tip (AT) position of the distal end of a catheter. Using data from the Virtual Tip (VT) 905 and the imaging and synchronization module 701, the CGCI system controller 501 determines the position error, which is the difference between the actual tip position (AP) and the desired tip position (DP). In one embodiment, the controller 501 controls electromagnets to move the catheter tip in a direction selected to minimize the position error (PE). In one embodiment, the CGCI system controller 501, provides tactile feedback to the operator by providing force-feedback to the VT 905.

FIG. 1A is a block diagram of a surgery system 503 that represents one embodiment of the CGCI system 1500. The system 503 includes the controller 501, a radar system 1000, a Hall effect sensor array 350 and a hydraulically-actuated system 1600. In one embodiment, the sensor 350 includes one or more Hall effect magnetic sensors. The radar system 1000 can be configured as an ultra-wideband radar, an impulse radar, a Continuous-Wave (CW) radar, a Frequency-Modulated CW (FM-CW) radar, a pulse-Doppler radar, etc. In one embodiment, the radar system 1000 uses Synthetic Aperture Radar (SAR) processing to produce a radar image.

In one embodiment, the radar system 1000 includes an ultra-wideband radar such as described, for example, in U.S. Pat. No. 5,774,091, hereby incorporated by reference in its entirety. In one embodiment, the radar 1000 is configured as a radar range finder to identify the location of the catheter tip 2. The radar 1000 is configured to locate reference markers (fiduciary markers) placed on or in the patient 390. Data regarding location of the reference markers can be used, for example, for image capture synchronization 701. The motorized hydraulically and actuated motion control system 1600 allows the electromagnets of the cylindrical coils 51AT and 51DT to be moved relative to the patient 390.

In one embodiment, the use of the radar system 1000 for identifying the position of the catheter tip 2 has advantages over the use of Fluoroscopy, Ultrasound, Magnetostrictive sensors, or SQUID. Radar can provide accurate dynamic position information, which provides for real-time, relatively high resolution, relatively high fidelity compatibility in the presence of strong magnetic fields. Self-calibration of the range measurement can be based on time-of-flight and/or Doppler processing. Radar further provides for measurement of catheter position while ignoring "Hard" surfaces such as a rib cage, bone structure, etc., as these do not substantially interfere with measurement or hamper accuracy of the measurement. In addition, movement and displacement of organs (e.g., pulmonary expansion and rib cage displacement as well as cardio output during diastole or systole) do not require an adjustment or correction of the radar signal. Radar can be used in the presence of movement since radar burst emission above 1 GHz can be used with sampling rates of 50 Hz or more, while heart movement and catheter dynamics typically occur at 0.1 Hz to 2 Hz.

In one embodiment, the use of the radar system 1000 reduces the need for complex image capture techniques normally associated with expensive modalities such as fluoroscopy, ultrasound, Magnetostrictive technology, or SQUID which require computationally-intensive processing in order to translate the pictorial view and reduce it to a coordinate data set. Position data synchronization of the catheter tip 2 and the organ in motion is available through the use of the radar system 1000. The radar system 1000 can be used with phased-array or Synthetic Aperture processing to develop detailed images of the catheter location in the body and the structures of the body. In one embodiment, the radar system 1000 includes an Ultra Wide Band (UWB) radar with a relatively high resolution swept range gate. In one embodiment, a differential sampling receiver is used to effectively reduce ringing and other aberrations included in the receiver by the near proximity of the transmit antenna. As with X-ray systems, the radar system 1000 can detect the presence of obstacles or objects located behind barriers such as bone structures. The presence of different substances with different dielectric constants such as fat tissue, muscle tissue, water, etc., can be detected and discerned. The outputs from the radar can be correlated with similar units such as multiple catheters used in Electro-Physiology (EP) studies while detecting spatial location of other catheters present in the heart lumen. The radar system 1000 can use a phased array antenna and/or SAR to produce 3D synthetic radar images of the body structures, catheter tip 2, organs, etc.

In one embodiment, the location of the patient relative to the CGCI system (including the radar system 1000) can be determined by using the radar 1000 to locate one or more fiduciary markers. In one embodiment, the data from the radar 1000 is used to locate the body with respect to an imaging system. The catheter position data from the radar 1000 can be superimposed (synchronized) with the images produced by the imaging system. The ability of the radar and the optional Hall effect sensors 350 to accurately measure the position of the catheter tip 2 relative to the stereotactic frame allows the controller 501 to control movement of the catheter tip.

Figure 2:
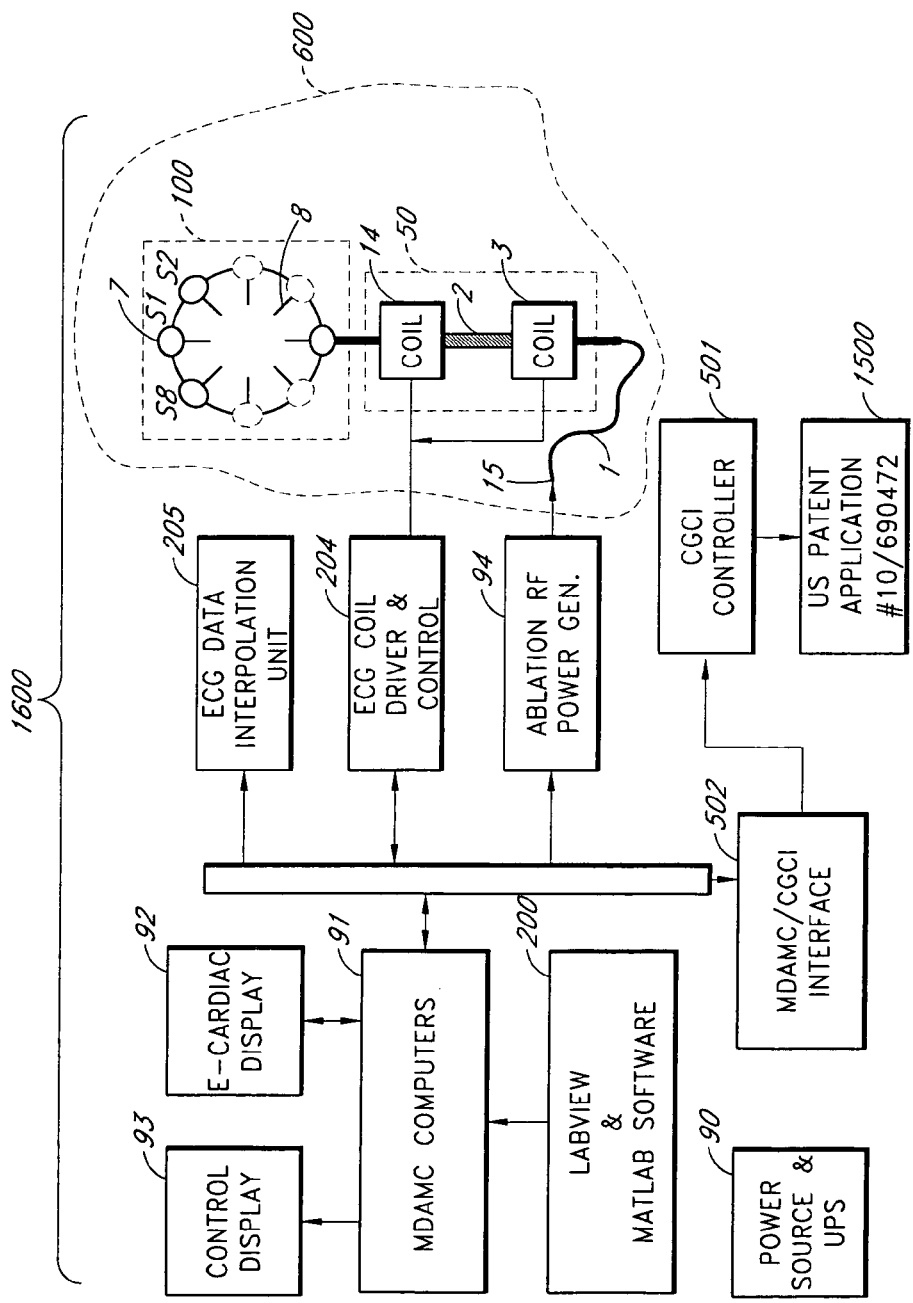
FIG. 2 is a block diagram of the mapping and ablation control and mapping system.

FIG. 2 is a functional block diagram of the magnetically-deployable electrocardiographic (ECG) and RF ablation catheter (MDAMC) and its associated supporting equipments. The system 1600 includes a catheter assembly, having an electrocardiographic and ablation tool. An ECG sensor head 100 includes eight MOSFET sensors 7 ($S_1$, $S_2$, $S_3$, $S_4$, $S_5$, $S_6$, $S_7$, $S_8$) and eight RF antennas 8, a coil 3, and its counterpart coil 14 (forming the magnetic mechanism), an elongated catheter body having a proximal end and an internal longitudinal lumen 1, and a bus wire harness 15. The tool is connected via the bus wire 15 to the ECG coils 3 and 14 driver and control 204. The electrocardiographic mapping and ablation catheter is provided to an ECG data interpolation unit 205. Data analyzed by the ECG interpolation unit 205 is used by the ablation RF power generator 94 which activates the RF antennas 8. The information generated by the ECG probe is provided to the application specific computer 91 with its software 200 made by National Instruments and MATH-LAB processing software used to control the probe to display its findings on the control display 93, as well as the electro-cardiac display 92. The system is powered by a Uninterrupted Power Supply 90.

In one embodiment, a diagnostic method employed by the magnetically deployable mapping and ablation catheter (MDAMC) is statistically based on correlating electrical activity with anatomical features which further allows the practitioner to evaluate certain patterns. In one embodiment, a biophysical model is used with the electrophysiological outputs to cardiac function as well as to the waveform obtained to form a map or maps of the cardiac wave. The data points measured by the sensor 100 with its MOSFET devices 7 coupled with the wavefront characterization as defined by the Poynting Energy Vector (PEV) 49, are analyzed and graphically represented using the control display 93 and the e-cardiac display 92. Correlating the electric generator during the depolarization phase in the cardiac model is related to the fact that surface-carrying elementary current dipoles (from the cellular ion kinetics across membranes) imply the subsequent avalanche (wavefronts) as it progresses through the myocardium (see e.g., A. Van OOsterom "Source Modeling of Bioelectric Signals", Proc. 3-ed, Rayner Granit Symposium (J. Malmivno ed.) Vol. 8-6, pp 27-32 1994).

Figure 1B:
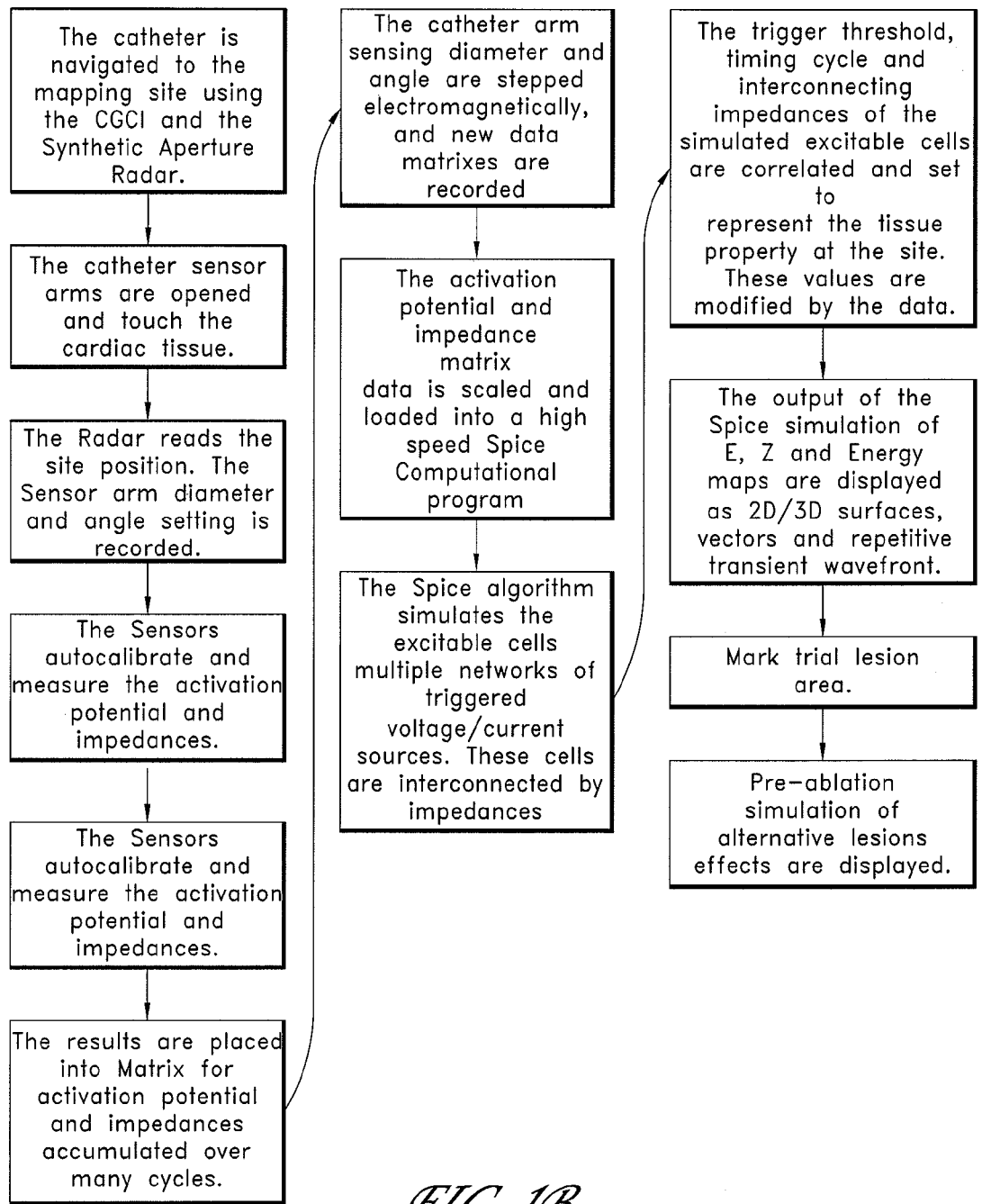
FIG. 1B is a flow chart of the process for conducting an ablation procedure using the CGCI system that includes a radar system, Hall Effect sensors and the mapping and ablation apparatus.

FIG. 1B is a flow chart of the process for conducting an ablation procedure using the CGCI system that includes a radar system, Hall Effect sensors and the mapping and ablation apparatus. In one embodiment, the catheter is navigated to the mapping site using the CGCI and the Synthetic Aperture Radar. The catheter sensor arms are opened and touch the cardiac tissue. The radar reads the site position, and the sensor arm diameter and angle setting is recorded. The sensors then autocalibrate and measure the activation potential and impedances. The results are placed into the matrix created for activation potential and the matrix created for impedances; the results are accumulated over many cycles. The diameter and angle of the catheter is detected and then both are increased electromagnetically, and new data matrixes are recorded at the new diameter and angle. The activation potential and impedance matrix data is scaled and loaded into a high speed Spice computational program. The trigger threshold, timing cycle and interconnecting impedances of the simulated excitable cells are correlated and set to represent the tissue property at the site. These values are modified by the data. The output of the Spice simulation of the E vector map, the impedance map, and the Energy map are displayed as 2D/3D surfaces, vectors and repetitive transient wavefronts. Then the user marks a trial lesion area. Then the system displays the effects of the pre-ablation simulation of the trial lesion.

FIG. 2 is a functional diagram of the main attributes which will become clear for those familiar with the art as will reading the descriptions and ensuing objects noted by the drawings which accompany them.

Figure 3:
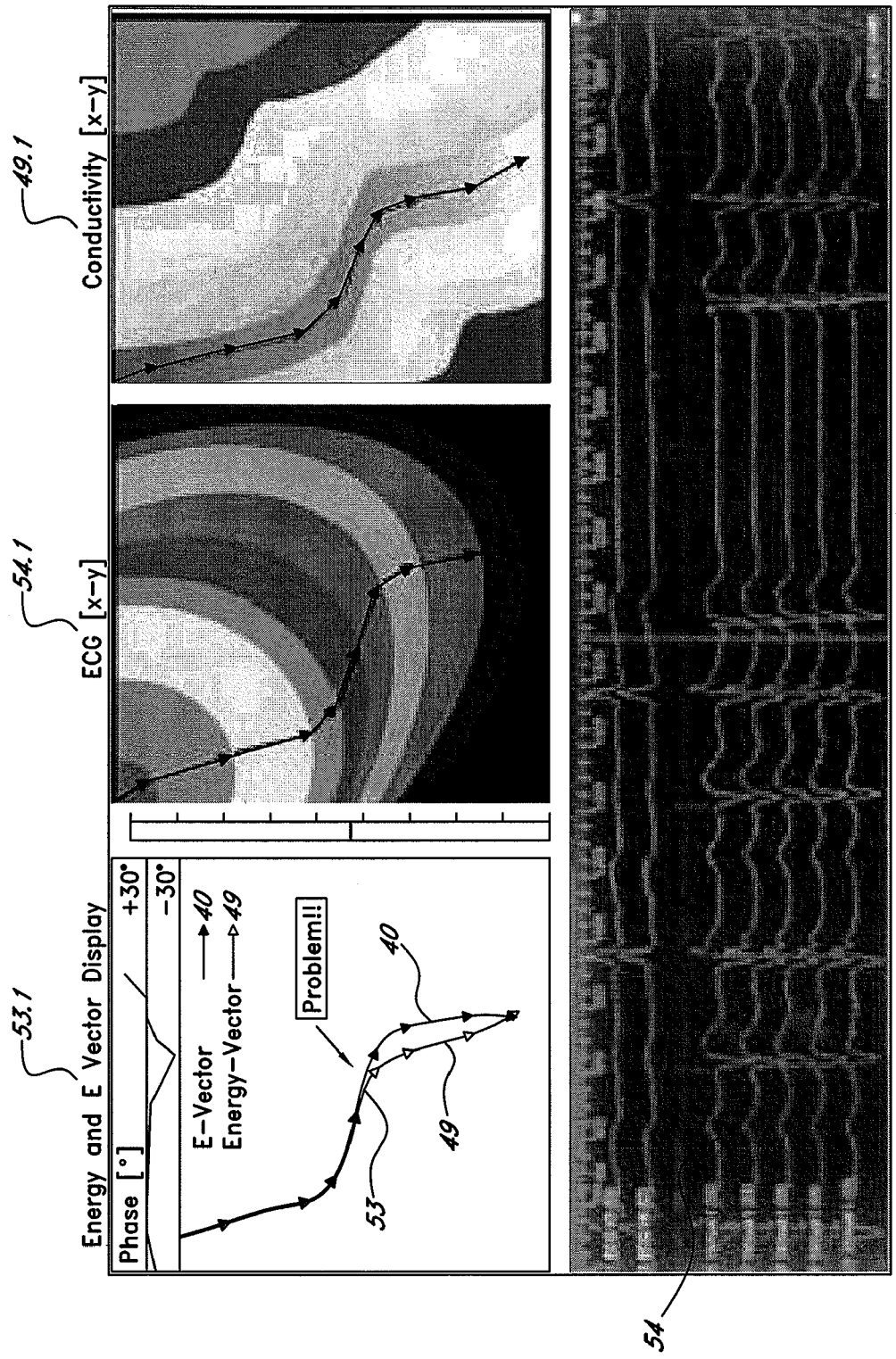
FIG. 3 shows computer-generated and E-cardiac images including: an ECG graph with its corresponding ECG plot on an x-y plane; a conductivity map represented on the x-y plane; and a composite energy and E-vector display.

FIG. 3 shows the wavefront showing the Poynting Energy Vector (PEV) 49 measuring the electrical potential and interpretation of the electrical activity as well as mapping of such wavefront propagation. In one embodiment, a mathematical algorithm is used for interpolation so as to achieve a relatively coherent view of the activation path while deriving a set of secondary measurable values such as Electric Heart Vector (EHV), Magnetic Dipole (MHV) as well as impedance measure of the myocardium wall.

The first assumption this method used is that cardiac activation spread is a relatively energetic event. It is further assumed in this model that in addition to the dynamic variations of electrical potentials during de-polarization and re-polarization of the excitable cell of the heart, a spread of electro magnetic energy is observed as the activation avalanches.

In one embodiment, the system measures both the electric and magnetic fields during cell activation, (model relationship of normal activation sequences and degree of inter individual variability is detailed, for example, in K. Simelius et al, "Electromagnetic Extra cardiac fields simulated with bidomain propagation model," Lab of Biomedical Engineering, Fin-02015, Hut, Finland, hereby incorporated by reference).

The dynamic spread of the energy contained in the electric and magnetic fields are then described by the use of Maxwell equations as applied to the conduction system of the individual rather than reproducing the anatomical variation that leads to anisotropic myocardium. This "energy model"

approach provides for calculation of the dynamic spread of energy contained in the electric and magnetic fields and respectively in the multisource excitable cells of the heart's myocardium region to be represented and hence mapped without the assumptions of idealized models.

The data analysis and extraction of diagnostic as well as pathological information can be mapped as a superimposed electric and energy wave.

To overcome the measurement limitations of myocardial anisotropy, and due to production of slam magnetic fields during an activation sequence, the algorithm and apparatus is able to regain the detection capability of a magnetic dipole (MHV) by the use of another vector derived from Maxwell's equations, the Poynting Energy Vector (PEV) 49.

Clinical observations reported that measuring the angle between vectors of equivalent electric dipole (electric heart vector, EHV) and magnetic dipole (Magnetic Heart Vector) provides significant corollary information about the myocardium conductivity. The overall anisotropic case of the myocardium conductivity is represented by a tensor. The degree of anisotropic conductivity manifestation is characterized by an angle along the transversal and axial conductivity paths.

The solution for measuring and deriving the relationship between the Electric Heart Vector (EHV) and its respective magnetic dipole vector (MHV), (hence, supplementing the analytical mapping with additional information about the myocardium conductivity and anistrophy), is derived from Maxwell's equation as the Poynting Energy Vector (PEV) 49. The PEV is constructed from the multiple potential and impedance vectors of the measurements. In one embodiment, a magnetically-deployable mapping and ablation catheter using MOSFET is used for potential sensing. A matrix arrangement for phase rotation for RF generation and the angle β between the PEV and EHV is used to infer the features of anisotropy in the myocardium. The anisotropy of the conductivity is uniform, hence activation energy change generated and consumed by the ionic diffusion process is within the activation region of the measurement. Thus, the volume integrations is accurate, with a margin of error reduction based on two independent techniques, one statistical (monte carlo) and Tikhonov regularization filtering.

In one embodiment, the law of energy conservation is used for the time period of the two QRS cycle (e.g., 1152 data measurements) to acquire the initial baseline data foundation to form the map.

The validity of the Poynting Energy Vector (PEV) 49 derivation is corroborated by the fact that the activation spread obeys the mathematical identity that the Poynting Energy Vector (PEV) 49 is directly exhibiting the E and B fields phase angle relationship. The integral form of Maxwell's equations leads to the Poynting Energy Vector (PEV) 49, and to the substitution of E and Z derivations of this vector.

Maxwell's second set of time varying equations can be written as:

$$\nabla \times E = -\frac{dB}{dt} \quad (1)$$

and $$\nabla \times B = \zeta\mu \frac{dB}{dt} + \mu J \quad (2)$$

By multiplying B and E respectively and subtracting Equation (2) from Equation (1) and using vector identities yields $$B \cdot (\nabla \times E) = -B \cdot \frac{dB}{dt} \quad (3)$$

and $$E \cdot (\nabla \times B) = \zeta\mu\left(E \cdot \frac{dE}{dt}\right) + \mu(E \cdot J) \quad (4)$$

Subtracting, rearranging and using vector identities yields.

$$\nabla \cdot (E \times B) = B \cdot (\nabla \times E) - E \cdot (\nabla \times B) \quad (5)$$

$$\nabla \cdot (E \times B) = -\frac{d}{dx}\left(\frac{1}{2}B \cdot B\right) - \frac{d}{dx}(\zeta\mu E \cdot E) - \mu JE \quad (6)$$

$$\nabla \cdot \left[\left(\frac{1}{\mu}E \times B\right)\right] + \frac{d}{dx}\left[\frac{\zeta}{2}E^2 + \frac{1}{2\mu}B^2\right] + J \cdot E = 0 \quad (7)$$

Integrating both sides of Equation (7) over the volume V and within the boundary Y gives:

$$\int_Y \frac{1}{\mu}(E \times B) \cdot dS + \frac{d}{dx}\int_V\left(\frac{\zeta}{2}E^2 + \frac{1}{2\mu}B^2\right)d\tau + \int_V (J \cdot E - \sigma E^2)d\tau = 0 \quad (8)$$

Equation (8) is a representation of the energy equation in which the first term (8.1) is the energy flux out of Y boundary of V. The second term (8.2) is the rate of change of the sum of the electric and magnetic fields. The third term (8.3) is the rate of work within V done by the fields on the ionic charges.

The last term in Equation (8) assumes the inclusion of the energy of the multiple sources of cell, ionic charge exchanges, thus:

$$\int_Y \frac{1}{\mu}(E \times B) \cdot dS + \frac{d}{dx}\int_V\left(\frac{\zeta}{2}E^2 + \frac{1}{2\mu}B^2\right)d\tau + \int_V (J \cdot E - \sigma E^2)d\tau = 0 \quad (9)$$

Equation (9) leads to the Poynting Energy Vector (PEV) 49 of $$E = \frac{1}{\mu}(E \times B) + s \text{ where } \nabla \cdot s = 0 \text{ (Poynting Energy Vector)} \quad (10)$$

The parameter of interest is the angle between the electric field and energy field. The vector E is obtained from energy vector from E field measurements by calculating the Z impedance vector.

By using the measured potentials $V_m$ and by employing Poisson equation, the E electric field is obtained:

$$\nabla \cdot \sigma \cdot \nabla V_m = 0 \text{ and } E = -\nabla V_m \quad (11)$$

Then, the Poynting Energy Vector (PEV) 49 can be written:

$$E = \frac{1}{\mu}\left((E\Box E)\cdot\frac{1}{Z} + c\right)\bar{n} \quad (12)$$

Where the E vector and impedance Z can be calculated from the measured data points.

One can further calculate the angle β between the E field and E energy vector, where the difference is such that:

$$90° - \alpha = \beta. \quad (13)$$

Figure 3A:
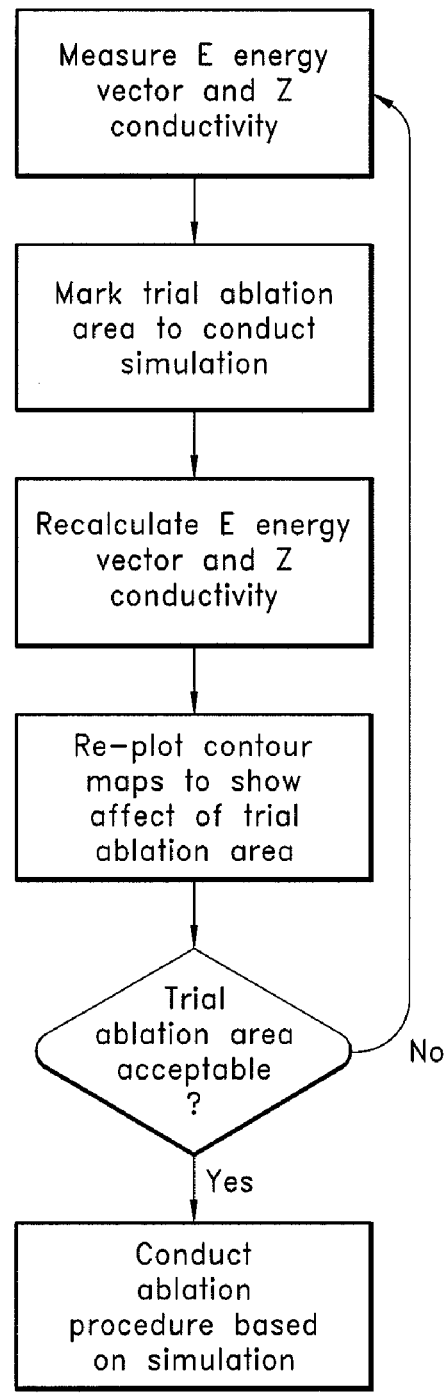
FIG. 3A is a flow chart of the pre-ablation simulation used to predict the ablation results prior to performing the actual ablation procedure.

A display of the E energy vector is useful for cardiac disorder identification. The E potential display serves a similar purpose as with other ECG systems, and the Z conductivity display is used to calculate the RF ablation power setting prior to the ablation procedure. FIG. 3A is a flow chart showing use of the pre-ablation simulation to verify the ablation results prior to performing the ablation procedure. In one embodiment, measurements 3000 of E energy data and Z conductivity data are collected from the electrocardiographic mapping and ablation catheter 600. This data is processed and displayed on a control display 93 and/or e-cardiac display 92. The user can mark a trial ablation area 3001 to conduct a simulation to verify the ablation results prior to performing the lesion. After the user marks the trial ablation area 3001, the system recalculates the E energy vector and Z conductivity to account for the hypothetical lesion, and determines the amount of RF energy that is necessary to create the lesion such that the desired conduction path is severed. Then the system displays the information 3002 on control display 93 and e-cardiac display 92. After analyzing the information, the user makes a decision 3003 as whether the user desires to repeat the process or conduct the ablation procedure based on the simulation.

The Poynting Energy Vector (PEV) 49 indicates that there is a flux of energy where E and B are simultaneously present. The spread of the energy flux in the case of Maxwell's derivation is further defined by the wave equation:

$$\nabla \times E = -\frac{dB}{dt} \quad (14)$$

taking the curl of each side $$\nabla \times \nabla \times E = -\frac{d}{dx}(\nabla \times B) \quad (15)$$

then $$\nabla(\nabla \cdot E) - \nabla^2 E = -\frac{d}{dx}\left(\varsigma\mu\frac{dE}{dt}\right) \quad (16)$$

Hence $$\nabla^2 E - \varsigma\mu\frac{\partial^2 E}{\partial t^2} = 0 \quad (17)$$

which is the wave equation.

In one embodiment, a simplified FEA program is used to extrapolate the energy wave for display.

The conditions for defining the actual material constants ςμ and the measured Z are related to Hadamord observation for a well posed problem so as to yield a solution for each data set.

FIG. 3 is a computer generated 91 and E-cardiac displayed 92 image comprising of 4 basic visual; an ECG graph 54 with its corresponding ECG plot and an x-y plane; a conductivity map represented on the x-y plane and a composite energy and E-vector display 53.1. The visual shown in FIG. 3 is the result of the observation that cardiac activation spread is an energetic event as defined by the formalism presented. The apparatus 1600 measure the cardiac activation spreads as an energetic event (using the MOSFET Sensor Head 100). The dynamic variations of electric potentials during de-polarization and re polarization of the excitable cells is measured, computed, and displayed as a spread of electromagnetic energy (as an activation avalanches). This energy is generated by the myriads of excitable cells and expands within the heart by propagating as an energy wavefront described by the formalism in Equation (17).

This wavefront propagation provides the clinician addition diagnostic information in addition to the prior art ECG measurements.

Deducing the magnetic heart vector (MHV) by using, at least in part, the energy heart vector PEV 49 is facilitated by the fact that the CGCI navigating and combining apparatus 501. By using the measured conductivity value and the corresponding ECG data, it is possible to derive the PEV 49 value which represent the energy heart vector (EHV), were E and Z is substituted for B. The apparatus 1600 measures and constructs the energy vector from the multiple potential and impedance vectors of the measurements and the algorithm for computing the PEV 49 and the EHV. The computer 91 and its software 200 such as, for example, LABVIEW and MATHLAB, can calculate and display the composite image of the energy vector 49 and the E-vector 40 shown as an image 53.1. From the angle between the PEV 49 and the EHV 40, the physician can infer the features of anisotropy in the myocardium. In summary, FIG. 3 shows the electrocardigraphic maps of the myocardium region with details of directly measured potentials on the endocardial surface. It further measures the surface potential and activation time matrix. The apparatus 1600 measures the conductivity-time matrix between the sensing points during activation. The composite display indicates the directional anisotropy between the sensing points during activation. The composite display shows the directional anisotropy between the electric potential vector and the energy vector for the cardiac disorder.

FIGS. 4, 4A, 4B, 4C and 4H are orthographic representations of the magnetically-deployable ablation and mapping catheter 600. An elongated catheter 1 body having a proximal end and an internal longitudinal distal end lumen. The catheter 1 is coupled to permanent magnet 2, forming part of the dynamic mechanism of the deployable sensor head assembly 50. The magnetically-deployable sensor head 50, includes a flange holder 5, which supports the semispherical dome 9, protecting the eight sensors 7, and their associated RF antennas 8, in a cluster as shown. The sensor head 50 extends towards catheter 1 body to form cylinder 9A which is received into a cavity 3 that is within the permanent magnet 2. The interior of cylinder 9A contains one or more spiral ridges 9B for engaging a screw, bolt or other device with corresponding spiral ridges. In one embodiment, arms 6 connect to a plurality of springs which connect to the deployable sensor head 50 such that the deployable sensor head 50 is in the closed state when the springs are relaxed. When the axial movement of coils 3 and 14 displaces the arm 6 (which holds the sensors 7 and the RF antenna 8) so as to form an "umbrella" with multiple deployment states (201, 202, and 203), the plurality of springs provide resistance to bias the arms 6 towards to the closed position. In one embodiment, arms 6 connect to a cable that allows the user to mechanically open and close the deployable sensor head 50 without the use of axial movement of coils 3 and 14.

Two coils 3 and 14 are shown as traveling on a guide rail 4. The assembly is further fitted with an irrigation tunnel 10, and a cooling manifold (not shown for clarity). The catheter 600 is further embedded with a conductive ring 13, forming the ground of the electrical circuit of the ablation and potential measurements (a feature which becomes clearer in the ensuing Figures).

FIG. 4A depicts the sensor head assembly 50, in its closed state where the antennas 8, are nested in the semispherical dome 9 and its function is explained in detail while comparing the intermediary state 202 and fully deployable state (the umbrella) shown in FIG. 4C. The relationships between the three deployable states; 201 closed, 202 intermediary and fully deployable state 203 in connection with the MOSFET sensor 7 measurements and the RF antenna 8 radiating mode are described.

The configuration shown in FIG. 4 where the irrigation tunnel is leading to the irrigation manifold 10, is used to provide a saline water solution so as to cool the radiating antennas 8, while improving the conductivity measurements 62 (impedance (Z)) during the ablation procedure.

FIG. 4B further shows the use of a guidewire 379, inserted through the tunnel cavity 10 (used for irrigation) so as to afford a safety measure to allow the catheter head 50 to be retrieved back to its closed state 201. In one embodiment, guidewire 379 screws into region 9B to connect to cylinder 9A. The safety procedure is such that when a power failure or debris collecting on the catheter (such as fat tissue, plaque, or a combination thereof) surfaces prevents retrieval of the antennas 8 to its closed state 201. The operator then inserts a guidewire 379 through the irrigation tunnel, engages cylinder 9A, and mechanically pulls the flange 5 back to its closed state.

FIGS. 4D and 4E show an improved catheter assembly 375 and guidewire assembly 379 to be used with the CGCI apparatus 1500. The catheter assembly 375 is a tubular tool that includes a catheter body 376 which extends into a flexible section 378 that possesses increased flexibility for allowing a more rigid responsive tip 2 to be accurately steered through a torturous path.

The magnetic catheter assembly 375 in combination with the CGCI apparatus 1500 reduces or eliminates the need for the plethora of shapes normally needed to perform diagnostic and therapeutic procedures. This is due to the fact that during a conventional catheterization procedure, the surgeon often encounters difficulty in guiding the conventional catheter to the desired position, since the process is manual and relies on manual dexterity to maneuver the catheter through a tortuous path of, for example, the cardiovascular system. Thus, a plethora of catheters in varying sizes and shapes are to be made available to the surgeon in order to assist him/her in the task, since such tasks require different bends in different situations due to natural anatomical variations within and between patients.

By using the CGCI apparatus 1500, only a single catheter is needed for most, if not all patients, because the catheterization procedure can be achieved with the help of an electromechanical system that guides the magnetic catheter and guidewire assembly 379 to the desired position within the patient's body 390 as dictated by the surgeon's manipulation of the virtual tip 905, without relying on the surgeon pushing the catheter, quasi-blindly, into the patient's body. The magnetic catheter and guidewire assembly 379 (e.g., the magnetic tip can be attracted or repelled by the electromagnets of the CGCI apparatus 1500) provides the flexibility needed to overcome tortuous paths, since the CGCI apparatus 1500 overcomes most, if not all the physical limitations faced by the surgeon while attempting to manually advance the catheter tip 2 through the patient's body.

The guidewire assembly 379 is a tool with a guidewire body 380 and a responsive tip 2 to be steered around relatively sharp bends so as to navigate a relatively torturous path through the patient. The responsive tips 2 of both the catheter assembly 375 and the guidewire assembly 379, respectively, include magnetic elements such as permanent magnets. The tip 2 includes permanent magnets that respond to the external flux generated by the electromagnets as detailed by patent application Ser. No. 10/690,472.

In one embodiment, the responsive tip 2 of the catheter assembly 375 is tubular, and the responsive tip 2 of the guidewire assembly 379 is a solid cylinder. The responsive tip 2 of the catheter assembly 375 is a dipole with longitudinal polar orientation created by the two ends of the magnetic element positioned longitudinally within it. The responsive tip 2 of the guidewire assembly 379 is a dipole with longitudinal polar orientation created by two ends of the magnetic element 2 positioned longitudinally within it. These longitudinal dipoles allow the manipulation of both responsive tip 2 with the CGCI apparatus 1500, as the electromagnet assemblies act on the tips 2 and "drag" it in unison to a desired position as dictated by the operator.

FIG. 4F illustrates a further embodiment of the catheter assembly 375 and guidewire assembly 379 to be used with the CGCI apparatus 1500. In FIG. 4F, a catheter assembly 310 is fitted with an additional two (or more) piezoelectric rings 311, and 312, located as shown. An ultrasonic detector in combination with the apparatus 1500 provides an additional detection modality of the catheter tip whereby an ultrasonic signal is emitted as to excite the two piezoelectric rings and provide a measure of rotation of the catheter tip relative to the North Pole axis of the magnet 2. With the aide of the computer, the CGCI apparatus 1500 is capable of defining the angle of rotation of the tip 2 and in the piezoelectric rings 311, 312 can provide additional position information to define the position, orientation, and rotation of the catheter tip 2 relative to the stereotactic framing available from the fiduciary markers 700AX and 700BX.

FIG. 4G is an orthographic representation of the catheter assembly 600 used for mapping and ablation. The catheter 600, in combination with the CGCI apparatus 1500, allowing the guidance, control, and imaging of the catheter 600 as it is push/pulled, rotated, or fixed in position. The catheter 600 includes an elongated catheter body 376 having a proximal end and an internal longitudinal distal end lumen, where a permanent magnet 2 (e.g., a magnet formed out of NbFe35 is used as the coupling elements for the CGCI apparatus 1500 in navigating the catheter 600 to its desired designation. The catheter is also fitted with assembly 50 (magnetically deployable mechanism) and sensor/antenna head assembly 100.

Figure 4H:
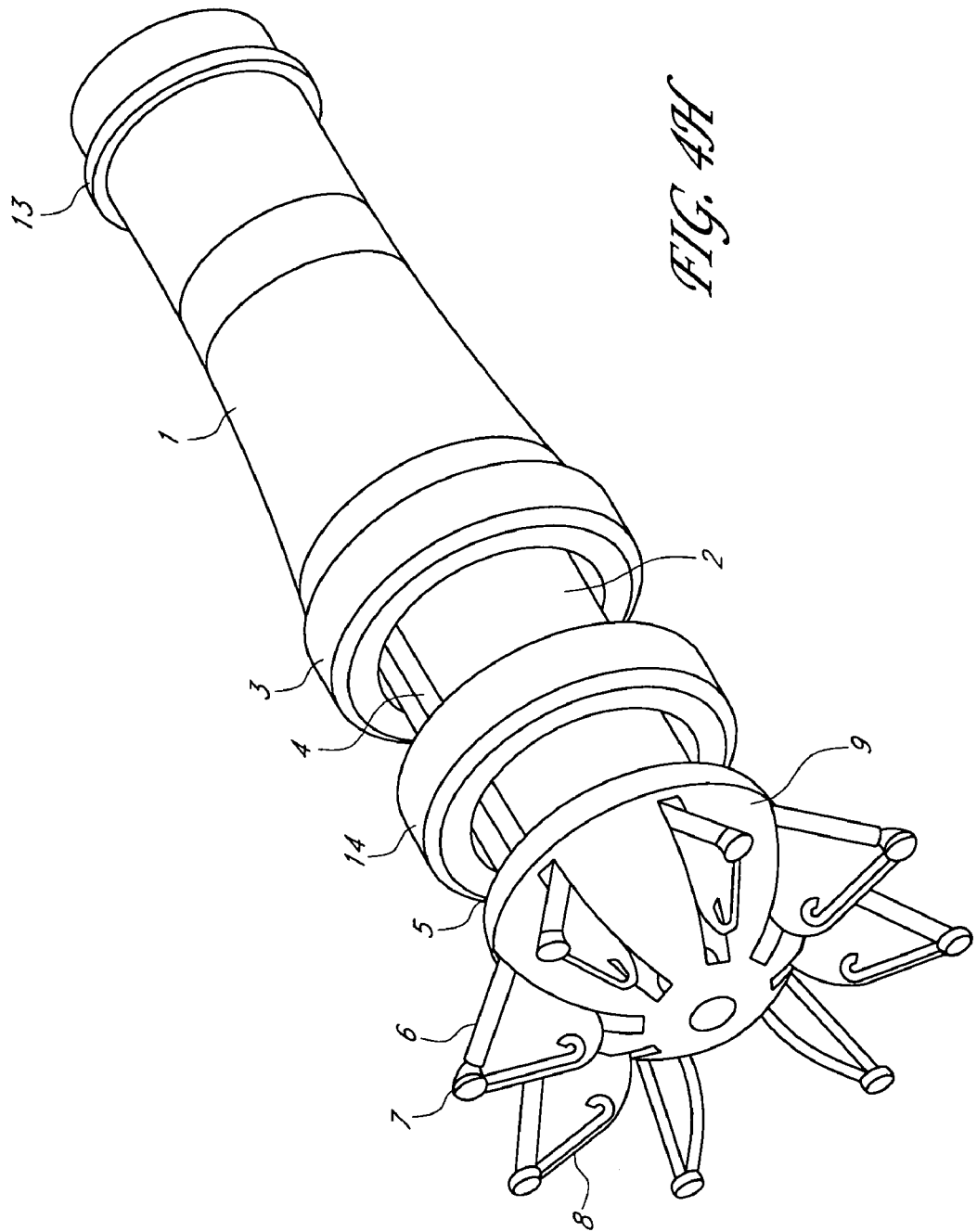
FIG. 4H shows an orthographic representation of the mapping and ablation catheter in a deployed state.
Figure 4I:
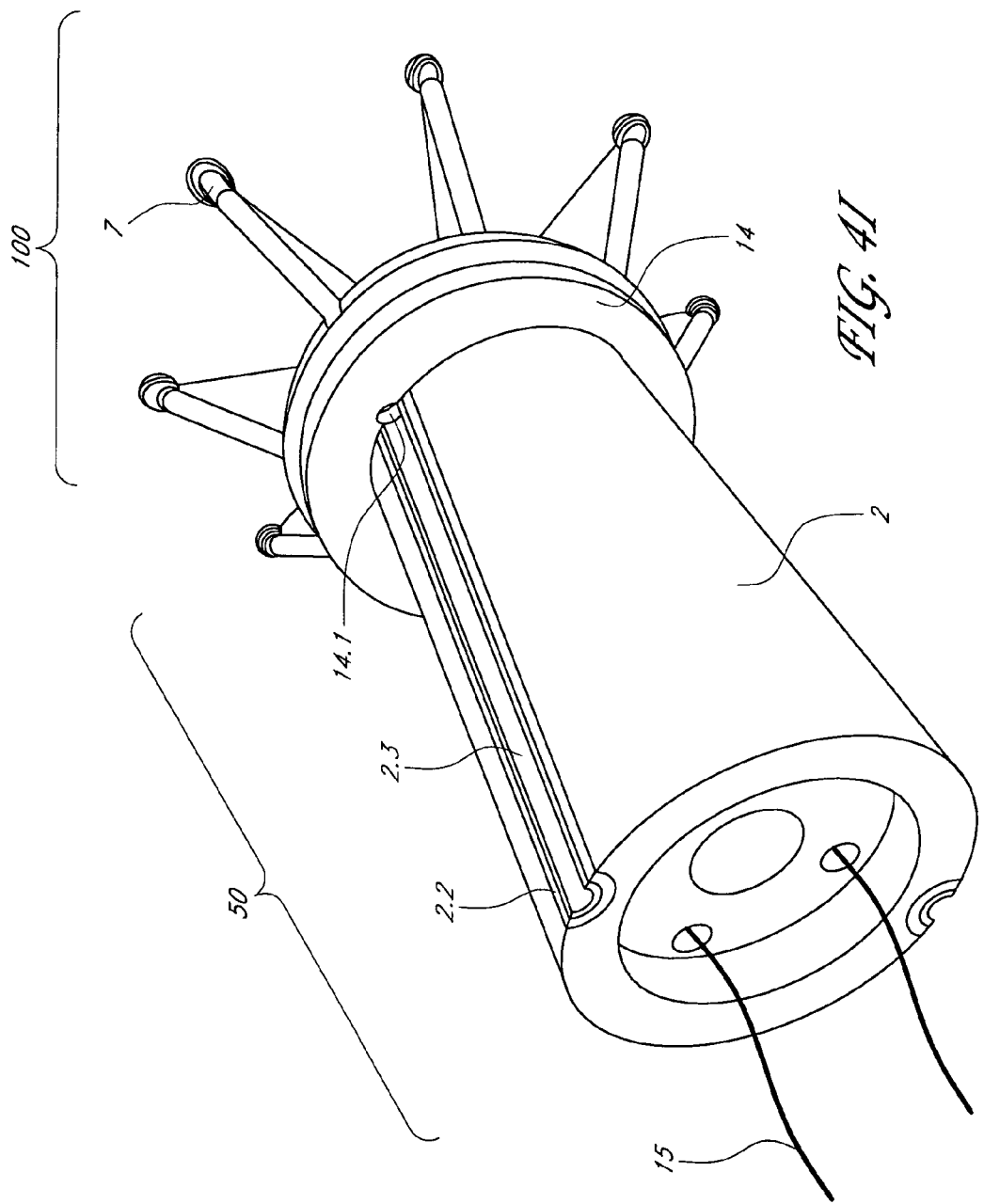
Figure 47:
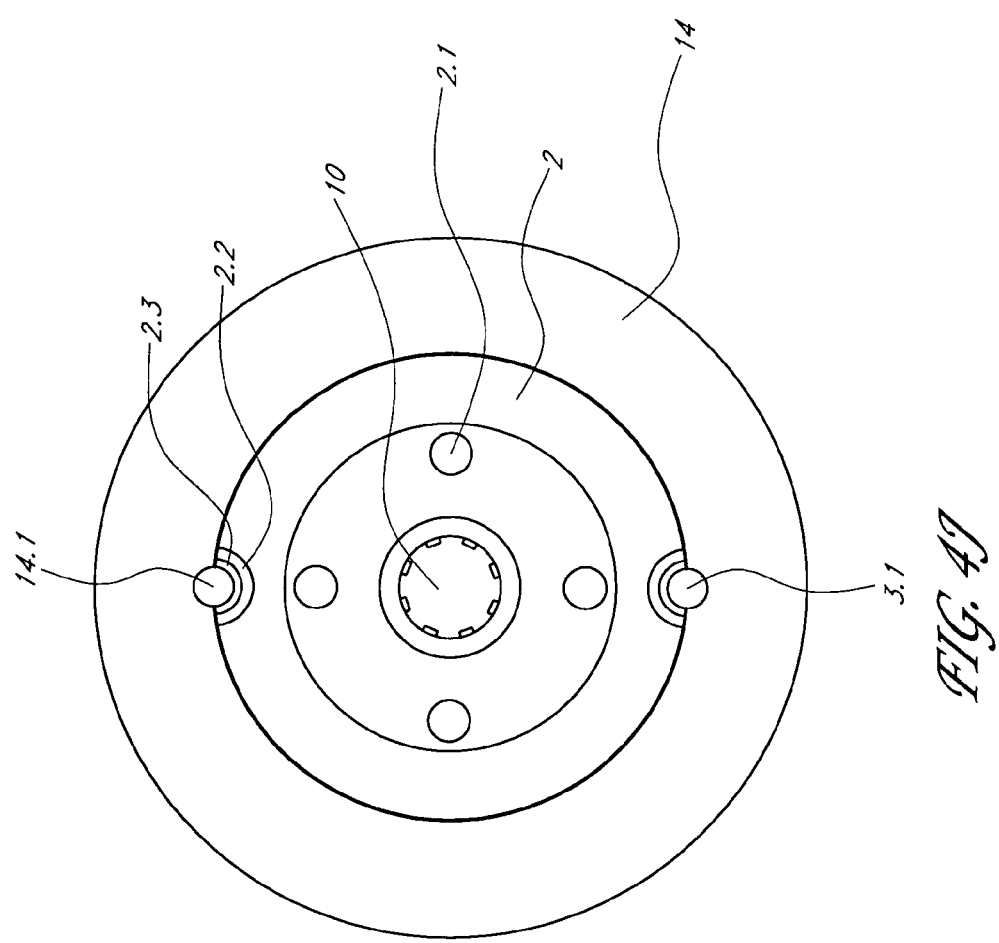

FIG. 4I shows the sensor head assembly 100 and the deployable magnetic mechanism 50. FIG. 4I also shows wiring and conduction elements forming the electrical circuit. A conductor 15 is threaded through a conductor 2.1 formed out of suitable polymer and is nested inside permanent magnet 2. The permanent magnet 2 is further modified to accommodate an electrical insulator 2.2 and an electrical ribbon 2.3. The coil electrical contact 14.1 travels over the ribbon 2.3 to form the "hot" lead (+) of the electrical circuit, while the return path (−) is the permanent magnet 2. Coil 14 and coil 3 (not shown for clarity) travels over the electrical ribbon 2.3 and similarly coil 3 travels over electrical ribbon 2.3 located 180° and electrical contact occurs when coil contact 3.1 is activated.

Figure 8:
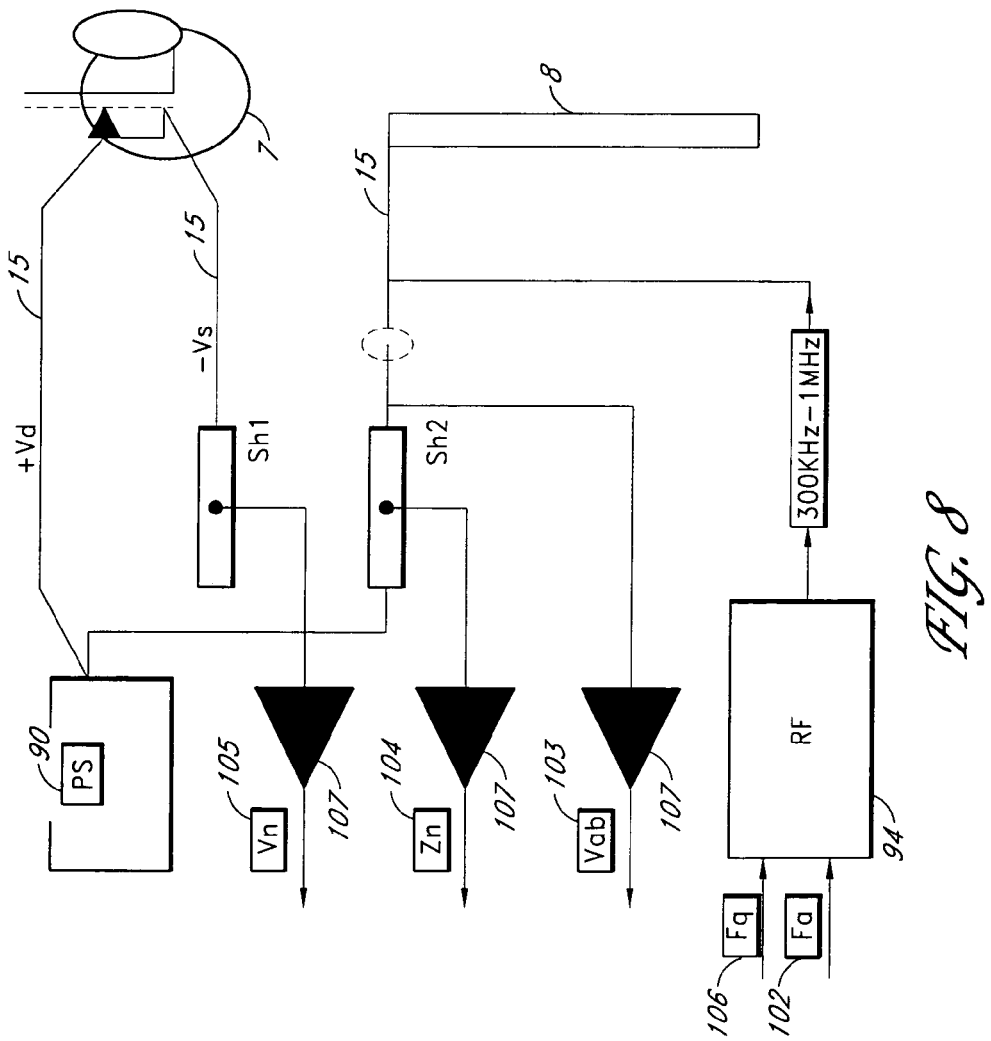
FIG. 8 is a schematic representation of the ablation tool and its attributes.

FIG. 4J is a cross sectional view of the catheter magnetic device 50 whereby, coil 14 is shown with its coil contact 14.1 and electrical ribbon 2.3 provide electrical connection between coil 14 and Power Supply 90 (shown in FIG. 8). The electrical isolation between the permanent magnet 2 and the electrical ribbon 2.3 is achieved with insulator 2.2. Further depicted are the conductor carriers (4 each) 2.1 and the irrigation tunnel 10.

Figure 4K:
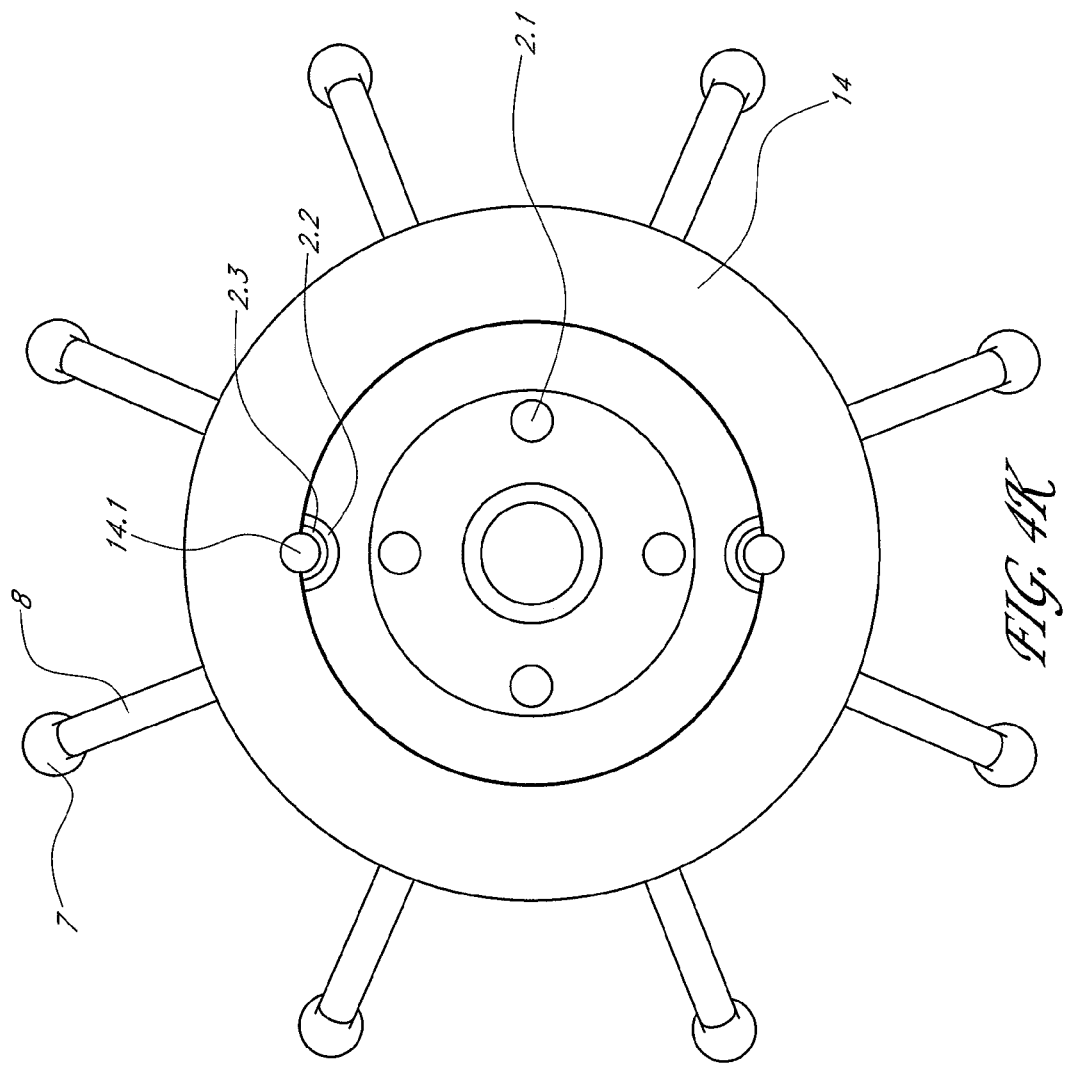

FIG. 4K shows a top view cross section of the MOSFET sensor head 100 (shown in FIG. 2) where the electrical wiring schematic is defined relative to the antenna 8 and the MOSFET sensor 7.

Figure 4L:
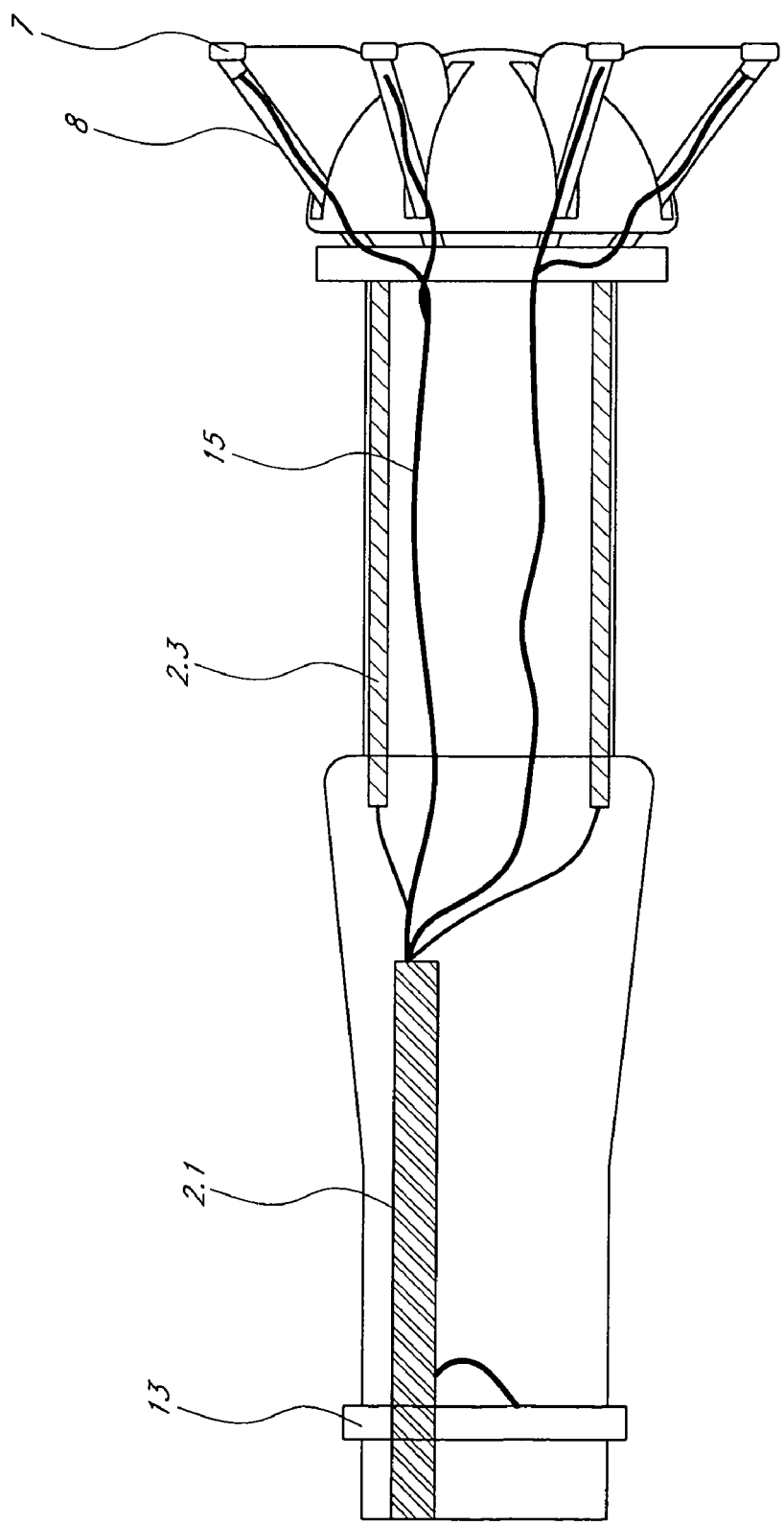

FIG. 4L is an orthographic depiction of the wiring and electrical circuit wherein conductor 15 pairs are connected to the antenna 8 and the MOSFET sensor 7. Electrical ribbon 2.3 with its conductors are threaded through conductor carrier 2.1. A ground path is provided to ground ring 13 to close the electrical circuit.

Figure 4M:
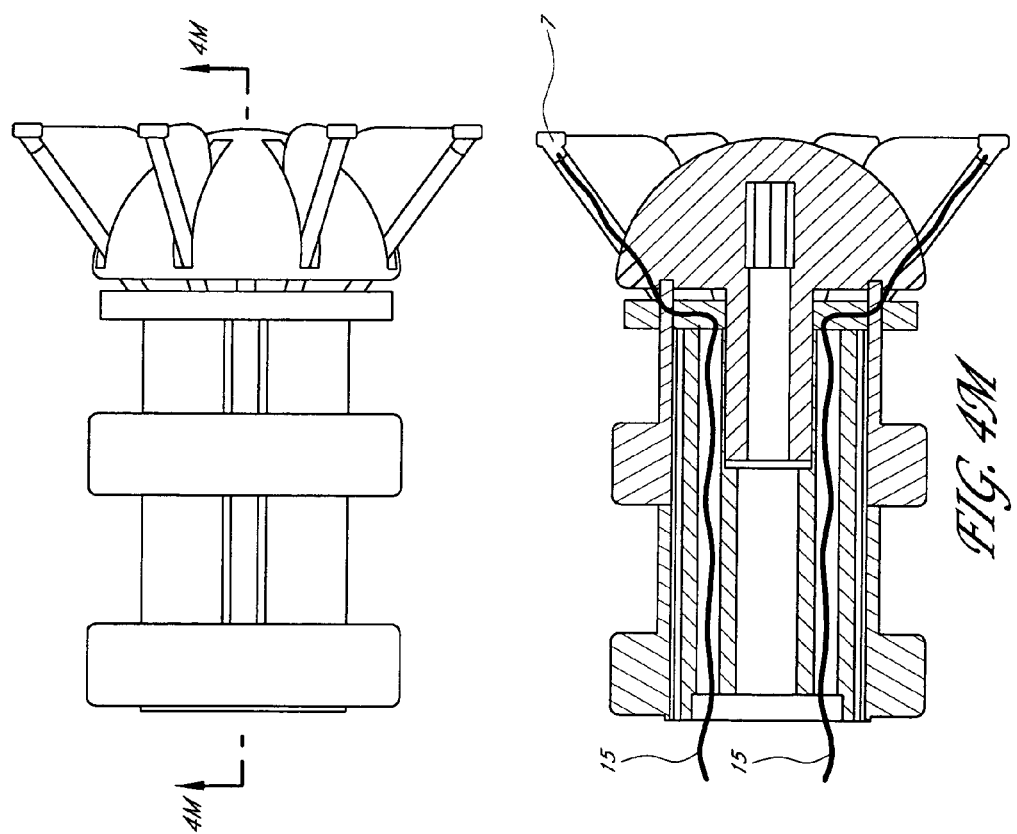

FIG. 4M provides a view and its cross section of the wiring layout for the sensor 1600.

Figure 5:
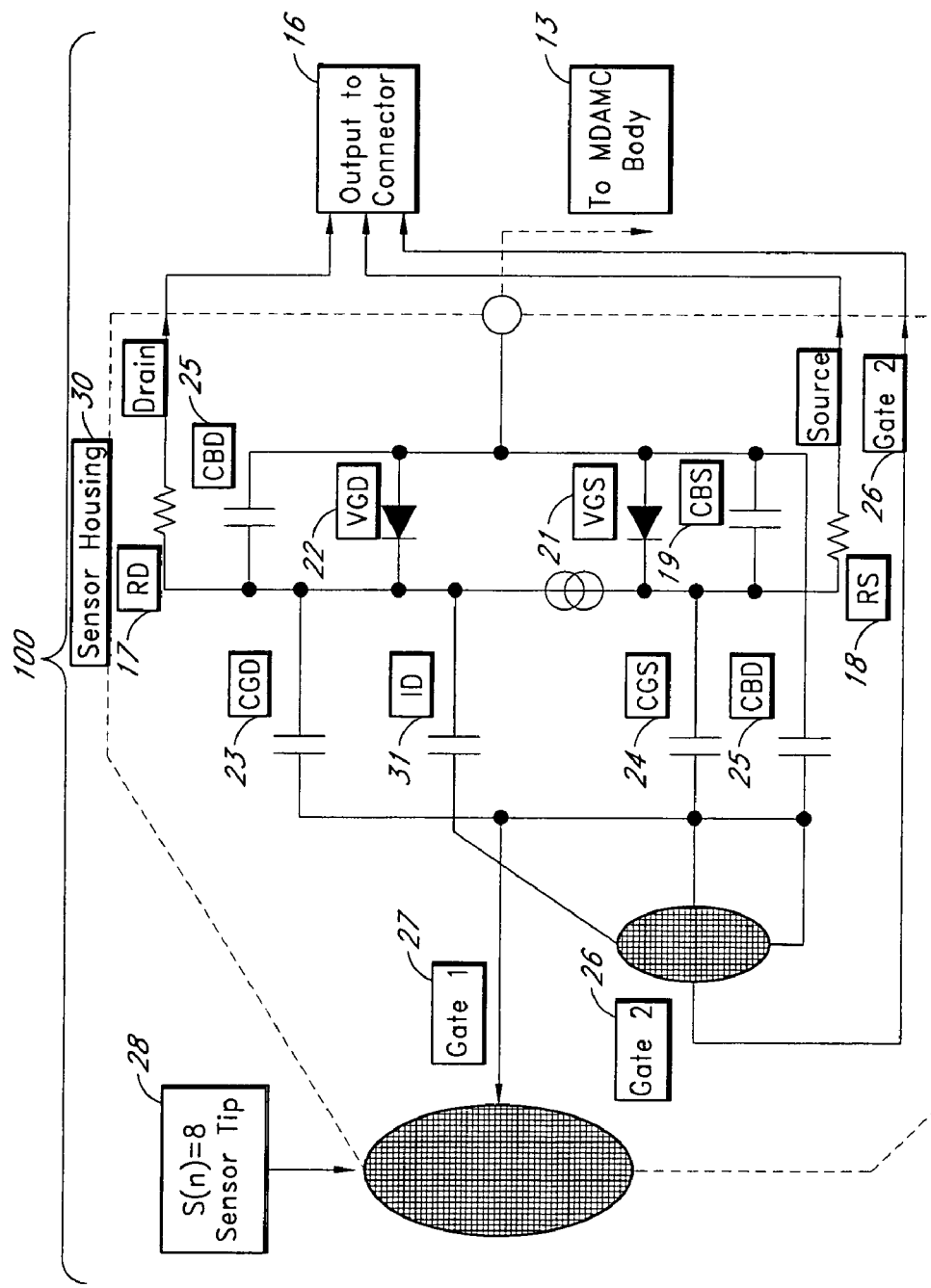
FIG. 5 is a schematic diagram of the MOSFET sensor used in measuring the electric potential.

FIG. 5 is an orthographic depiction of the internal equivalent circuit of the sensor array. In one embodiment, there are eight MOSFET sensors on the ablation and mapping apparatus 600.

The MOSFET potential sensing device is a junction field effect transistor that allows a current to flow which is proportional to an electric field, basically emulating a voltage-controlled resistor. The module 100 includes a resistor. The resistor RD 17, is a linear resistor that models the ohmic resistance of source. The charge storage is modeled by two non-linear depletion layer capacitors, CGD 23 and CGS 24, and junction capacitors CBD 25, CGD 23, and CBS 19. The P-N junctions between the gate and source and gate and drain terminals are modeled by two parasitic diodes, VGD 22, and VGS 21. Gate 1 of the MOSFET sensor tip 28 is item 27 and gate 2 of the MOSFET sensor assembly 100 is item 26. Gate 1 with reference designator 27 at the sensor tip S(n) (n=1, 2, 3, ... 8) is a relatively high impedance, insulated semiconductor structure. The device 100 behaves as voltage-controlled resistor. The potential between the gate structure 26, 27 and the drain-source structure (RS 18, RD 17) semiconductor substrate defines the transconductance of the output connections 16.

By connecting the drain-source 17, 18 structure to the sensor body 100, the potential reference for measurement is established. This reference is configured as a ring 13 along with the catheter body as shown. The measurement process of probe 100 is set to a zero voltage as the drain-source 17, 18 structure, the sensor's gate junction 27 assumes the tissue potential with a relatively small charging current flowing into the net parallel sum of the junction capacitors, CBD 25, CGD 23, and CGS 19. The drain-source 17, 18 voltages is then applied gradually to the device charging these capacitors from the outside power source, thereby "nulling" the current needed to form the gate so as to obtain the operating potential (about 6 VDC). The sensing procedure is relatively noninvasive to the cell as well as to the potential level and current drain of the probe 100 upon the cardiac tissue. Gate 2, item 27 provides a biasing input so as to provide a continuous active mode for the probe 100. This input is also used for self-calibration of the probe 100.

Figure 6:
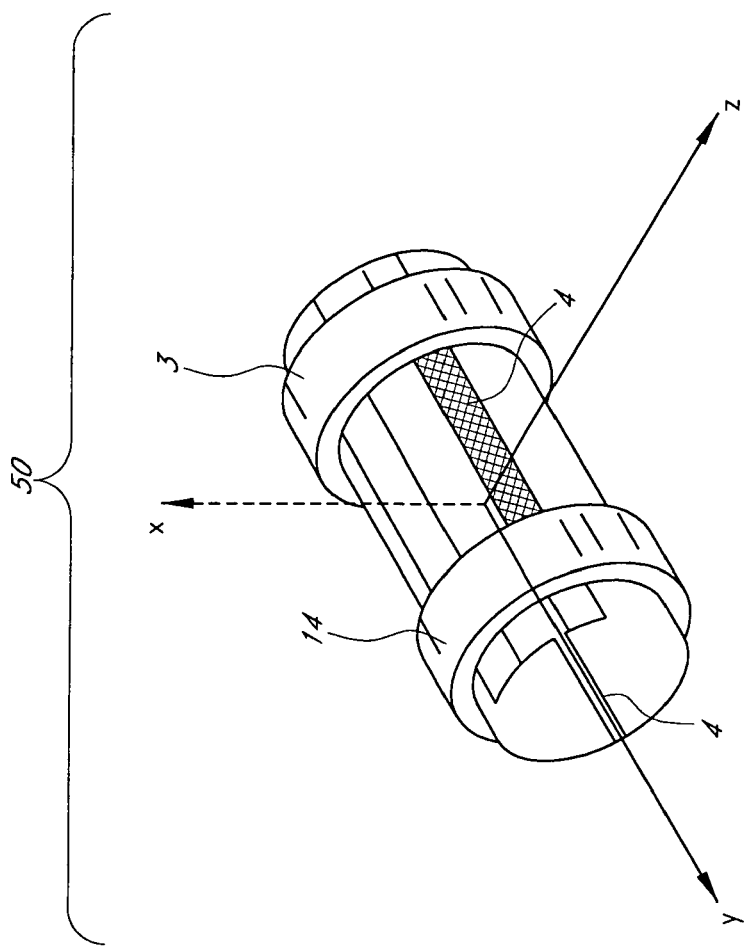
FIGS. 6, 6A, and 6B show the magnetically-deployable mechanism used to reduce the measurement error and increase the surface area of the measured event.
Figure 6A:
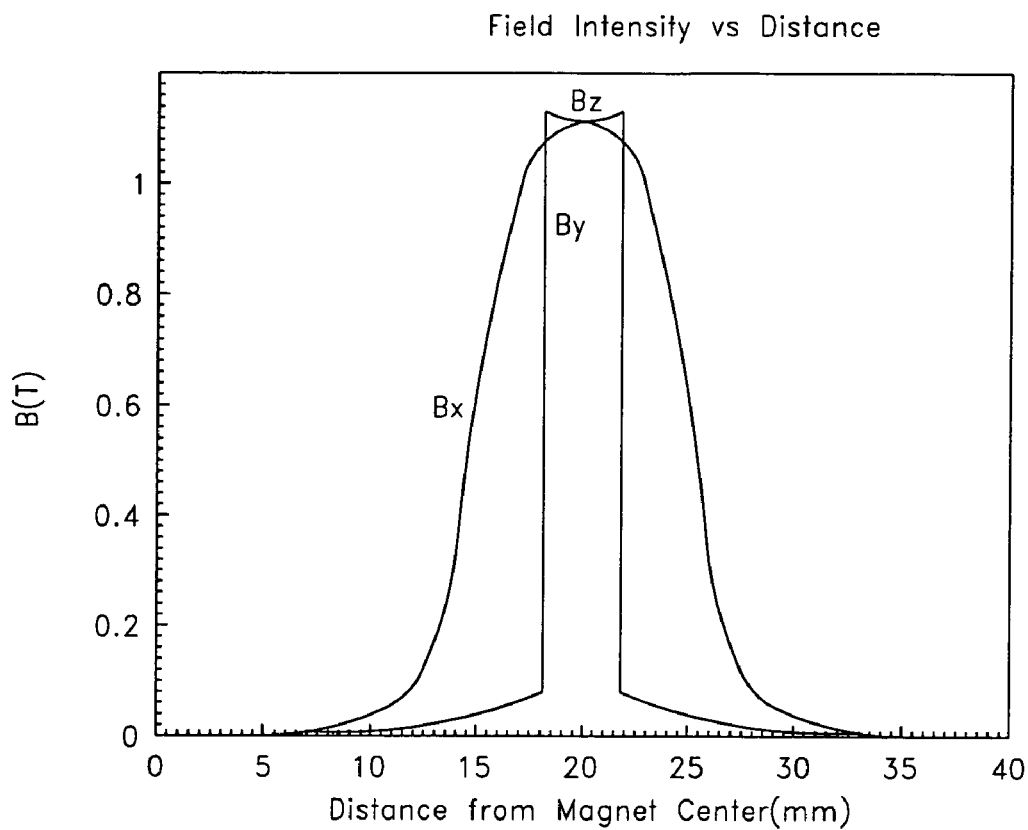
Figure 6B:
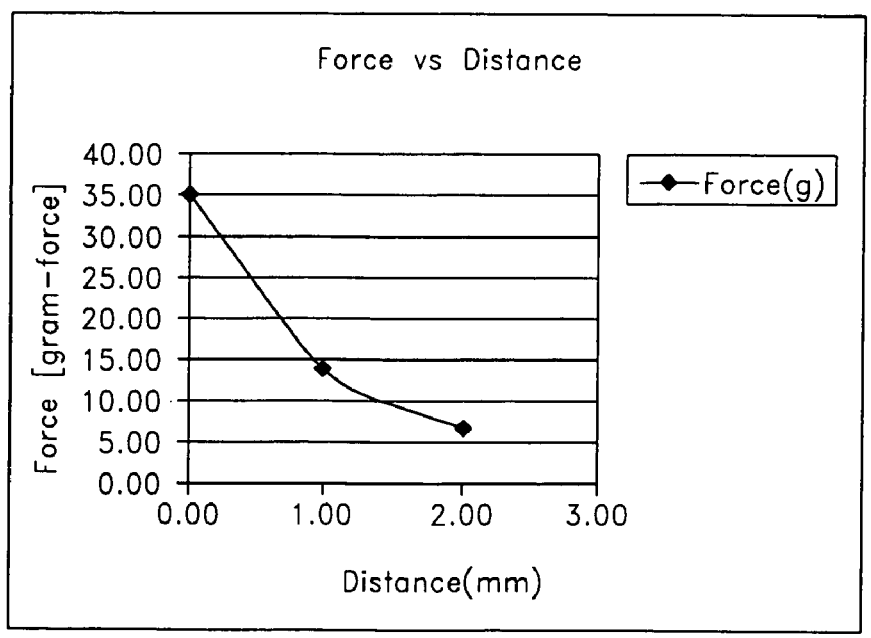

FIGS. 6, 6A, and 6B are isometric representations of the actuating mechanism of the magnetically-deployable ablation catheter 50 including the coil 3 and its counterpart coil 14 traveling axially on the permanent magnet 2 (NbFe35). In one embodiment, coil 3 and its counterpart coil 14 travel axially inside the permanent magnet 2. By applying a current, the coil moves toward or opposite to the N-S tips of the magnet Z. The magnitude of the coil currents define the position of the sensing head 100.

The ablation magnetic assembly 50 includes a 10 mm long and 3.8 mm diameter NbFe permanent magnet (item 2) and the coils 3 and 14. In one embodiment, the coils 3 and 14 carry an equivalent current of 200 ampere-turns maximum. The coils experience force along the "x" axis. The magnetic field strength is about 1.2 tesla at the tips. The forces on the coils range from approximately 0 to ±35 gram-force at approximately 100 mA current. Controlling the coil current magnitude and polarity sets the desired tool positions (states 201, 202, and 203). The field intensity along the axis in the permanent magnet 2, is charted by FIG. 6A. The travel and force (gram-force) of the assembly 50, along the axis "x" is shown by FIG. 6B.

The ablation sensor head 100 (including the MOSFET sensors 7 and RF antennas 8) travels along the "x" axis to form the measurements path, by providing an axial travel and opening the manifold to provide: activation state measurement and calibration 200, deployable state sensor head at intermediary state 202, and fully open state 203. The mechanical opening of the sensor head 100, to form various spatial positions (201, 202, and 203) allowing the apparatus to acquire the desired measurements on the same region during at least one or more QRS complex activation sequences and record the data points for relatively high fidelity measurements and error analysis techniques. The use of a magnetically-deployable mechanism to form the position during one or more QRS complex cycles further allows the apparatus to locate the electrical wavefront characteristics, so as to determine the geometry of the wavefront spreading through the myocardium.

A three-state measurement in the same region while detecting the electrical activity of the heart improves the measurements where signal quality is poor and provides more data points for construction of the isopotential lines. The error generated due to the abrupt change in potential is further reduced by the use of the deployable states. The deployable state positions allow the apparatus to acquire local features of the wavefront such as conduction velocity, potential gradient and/or breakthrough. A neighborhood of a relatively larger area during the activation sequence further provides for stability of the acquired measurement and the establishing of statistical significance of the wavefront event recording.

Figure 7:
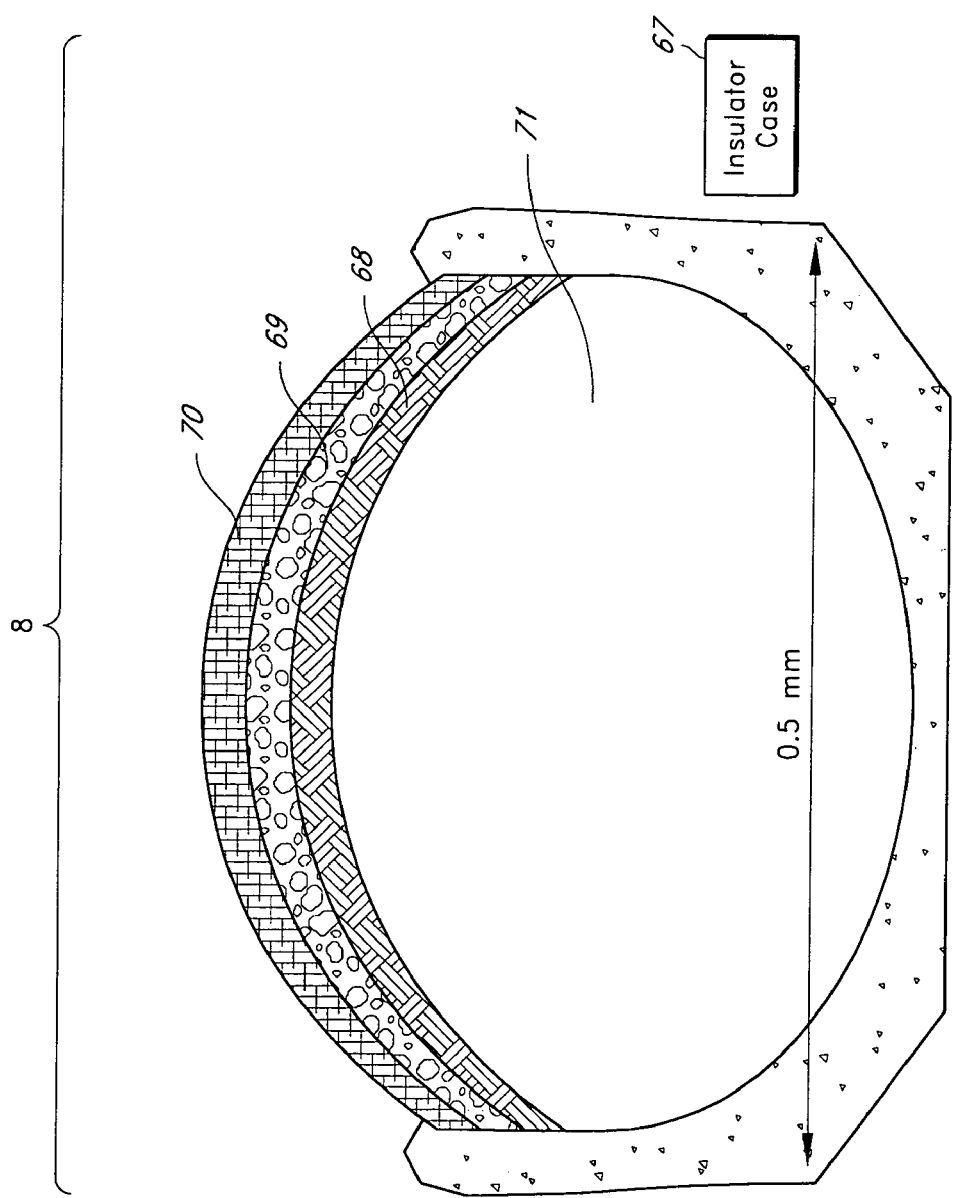
FIG. 7 is a cross-sectional view of the RF antenna.

FIG. 7 is a cross section view of the RF antenna 8 used in the ablation mapping apparatus. In one embodiment, there are eight antennas spaced around the sensor semispherical head 9. The antenna 8, serves two functions: it is an electrode that measures the tissue impedance (Z) between the antennas, and it is also serving as the RF ablation tool (the radiator).

The antennas 8 typically should not interfere with the measurements by injecting or draining the surface potentials 46. The functional requirements of the ablation and mapping probe is first to be conductive during the impedance tests (Z) 62, and the RF ablation, while the antennas 8 should in a relatively high-impedance state during the ECG mapping 60. In one embodiment, the antennas 8 are formed using, from N junction 68, and P junction 69, semiconductor (N-P junction).

The operational characteristics of the RF antennas 8 is such that during the relatively sensitive ECG potential tests where the controller 1600 activates the $S_1$ MOSFET through $S_8$ sensor (MOSFETS) the silver coating 70 of the antenna 8 is set in a reverse-biased mode. In the reverse biased mode (acting as a diode) leakage current is small (e.g., <1 µA). During the test mode, the tissue is interfaced with the antenna as an electrode where the junction is set in a forward-biased mode, to conduct the measuring current.

During the RF ablation mode 65, the antennas are set in dual modes of conduction 62 and radiation 63. There is a conductive path to the tissue through the forward biased P-N junction while applying the RF voltage, while the antenna also radiates 63. The arrangement of the antennas 8 are set in pairs so that the antennas receive P-N and N-P semiconductor layers, thus conduction symmetry is maintained. In one embodiment, the P-N layers are shaped around the edges where the conductive part of the antenna 8 meets the insulating case 67, to reduce uneven spot-heating. (The flow effects lesion formation during RF cardiac catheter ablation as the lesion dimensions and tissue heating are dependent not only on temperature but on other secondary conditions such as heat sinking of blood flow and impedance value of the tissues).

The antennas 8, radiate 63, about 6 W of RF power each and total radiating power 63 is approximately 48 W maximum.

FIG. 8 is an orthographic depiction of the mapping and ablation catheter 600 whereby power supply 94 is provided to the sensor 7 for measuring the electric potential on the interior cardiac surface, $V_n$ 105 which is a data set electric potential value $V_i$ at time $T_i$ forming a spatio-temporal manifold 704 ($V_i, T_i, X_i, Y_i, Z_i$) and calibration points 700AX and 700BX forming an electric map over the 704 grid (manifold). Amplifier 107 transmits a signal measured by the Sensor 7 to the data interpolation unit 205 which correlates the space temporal electric value anatomy on the map (s) which is generated and updated by the wavefront algorithm (e.g., using the Poynting Energy Vector PEV 49). In one embodiment, there are eight antenna arms 8 spaced around the central magnetic head 100, which are controlled so as to form at least three spatial states 201, 202, and 203 forming different aperture sizes. The antennas items 8 work during RF ablation in dual modes of conduction and radiation. The conductive path to the tissue through the forward biased P-N junction 68 and 69 during RF (300 kHz-1 MHz) voltage application 103 (performed by Amp 107 and RF generator 94). Antenna 8 also radiates in pairs (4 sets) where the antenna receive P-N and N-P semiconductor layers, thus conduction symmetry is maintained. Conductivity measurements and impedance values ($Z_n$) 104 are displayed so as to control the ablative energy. In one embodiment, the value of radiative energy is 6 W of RF power for each antenna with a total energy of approx. 48 W maximum.

During ablation the system 1600 generates RF energy which produces relatively small, homogeneous, necrotic lesions approximately 5-7 mm in diameter and 3-5 mm in depth. The system 1600 with its mapping and ablation catheter 600 is fitted with an irrigation tunnel 10 which sprays a saline water over the antennas to allow the ablation system to control the energy delivery and rapidly curtail energy delivery for impedance $Z_n$ (104) rise. The saline cools the antennas 8 which minimizes impedance rises and provides for creation of larger and deeper lesions. In one embodiment, the apparatus 1600 and its MDAMC computer 91 is provided with look-up-tables so as to afford a predetermined ablation geometry formation as a function of multiple parameters affecting the lesion geometry.

In one embodiment, the system 1600 is configured to target the slower pathway in AVNRT (the inferior atrionodal input to the atrioventricular (AV) node serves as the anterograde limb (the slow pathway). In the case of WPW (Wolff-Parkinson White Syndrome), the system 1600 is configured to ablate the accessory pathway which carries the WPW syndrome. In cases such as atrial flutter due to a large reentrant circuit in the right atrium a linear lesion of this isthmus cures this form of atrial flutter.

The ability of the ablation system 1600 to form a predefined lesion geometry is provided by the antenna 8 construction P-N, N-P doping and the ability of the generator 204 to vary the frequency (Fq) 106 and phase (Fα) 102 so as to afford a precision delivery of energy which forms the lesion.

In one embodiment, the system 1600 maps the breakthrough and potential while maintaining contact with the myocardium ($Z_n$), tissue desecration created by the RF energy (500 kHz) which causes a thermal injury such as desiccation necrosis. RF energy delivered by the antennas 8 located on the ablation head assembly 100 causes the resistive heating of the predefined geometry (linear, section circumference zig zag, etc.) of the tissue in contact with the antenna 8. Cooling the radiating antennas 8 is performed by the irrigation tunnel 10. In one embodiment, temperature is maintained at approx. 50° C.

FIGS. 9 and 9A show the ablation and mapping catheter 600 as it is introduced precutaineously into the heart chambers and sequentially record the endocardial electrograms for correlating local electrograms to cardiac anatomy. In one embodiment, the catheter is advanced by the use of magnetic circuits which are capable of generating a magnetic field strength and gradient field to push/pull and bend/rotate the distal end of the catheter 600 and as detailed by Shachar U.S. patent application Ser. No. 10/690,472 titled "System and Method for Radar Assisted Catheter Guidance and Control" hereby incorporated by reference. The catheter 600 is navigated and controlled locally with the aid of fluoroscopy and by the radar as it is detailed by the ensuing drawings and its accompanying descriptions.

In one embodiment, the catheter 600 is manually advanced into the heart chambers and sequentially recorded the endocardial electrograms, again using the radar and fiduciary markers for local definition of the site, while advancing the performing the mapping and ablation procedure.

FIG. 9 shows the catheter 600 as it is advanced through the heart chambers 390. FIG. 9A shows the catheter 600 in various deployable states. In one embodiment, during measurement, the manifold holding the sensor array 8 in the catheter 600, expands from a closed position state 201 to a deployable open state [umbrella]. At various open geometry states, sensor array 8 samples electrical potentials to create a set of data points. In one embodiment, the catheter in the deployable state forms a circular shape as the manifold expands to form various open geometry states. The intermediary open state 202 indicates an enlarged circumference and the fully deployable open state 203 represents the sensor array 8 in its maximum spatial coverage.

The intracardiac mapping is performed by measuring the electrical potential as it moves from state 201 through the state 202 and finally through the open state 203. The data is provided to the computer and processing functional unit 1600 which controls the procedures.

Figure 9B:
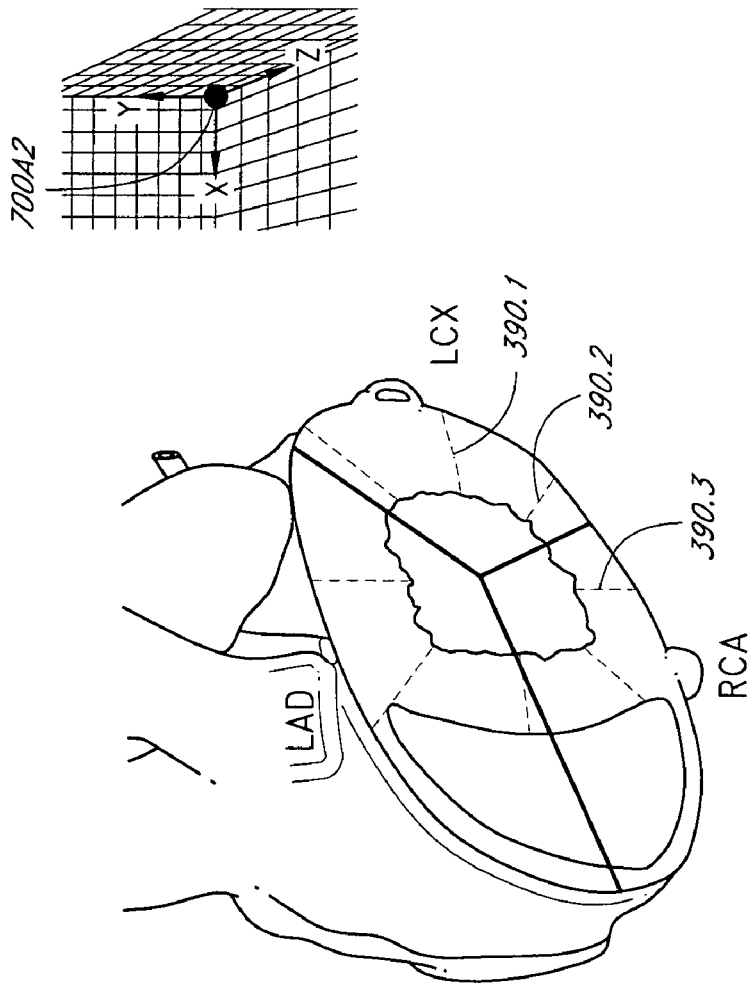
FIG. 9B shows the endocardial electrogram map resulting from sequential measurements of electrical potential detected by the catheter at various open geometry states.

FIG. 9B shows the endocardial electrogram map 54 resulting from sequential measurements of electrical potential detected by the sensor array 100 (including the MOSFET sensor 7 and antenna array 8) in the catheter 600 at various open geometry states 201, 202, 203. The conductivity data collected sensor array 8 is processed and graphically represented using the control display 93 and the E-cardiac display 92. In one embodiment, the conductivity data collected by sensor array 8 is displayed in a contour map 49.1 as depicted in FIG. 3, which also displays a contour map 54.1 of the ECG data, and a vector map 53.1 of the Energy and E Vector data. In one embodiment, contour map 49.1 of the conductivity data also graphically displays a previous ablation site 9004 from created from stored data generated from a previous ablation procedure. Previous ablation site 9004 represents an area of high impedance. In one embodiment, the location of previous ablation site 9004 is verified using the new data collected from sensor array 8 before previous ablation site 9004 is displayed in contour map 49.1.

FIG. 9B further depicts the fiduciary marker 700A1, 700A2, and 700B1 as shown on the dimensional grid providing the numerical x-y-z coordinate set for the catheter electrical, impedance, measurement performed using the catheter 600. Anatomical markers 390.1, 390.2, and 390.3 are noted on the grid and recorded as to their dimensional as well as clinical significance during the travel log of the ablation and mapping catheter 600. Further detail of the procedure by which catheter 600 acquires the electrical and conductivity data relative to dimensional as well as anatomical marker are described in FIG. 10.

The system 1600 with its mapping and ablation catheter 600 performs the tasks of mapping using the sensor array 100 as follows: calibration and position definition using radar 1000, cardiac morphology and geometry synchronization with images generated by x-ray fluoroscopy or MRI etc is established. (Synchronization methodology is provided by radar 1000 and fiduciary markers 700AX and as it is detailed by FIGS. 11 and 11A).

Data obtained from sensor array of catheter 600 is processed and its geometry and dimensional attributes are defined as to its physiological reference. Data of maps are stored relative to its fiduciary markers, so it can be retrieved and used during the ablation sequence.

The ablation catheter is then directed to its desired site. The wavefront characteristics are established using the Poynting Energy Vector (PEV) 49 and the reconstruction of the potentials and maps of the wavefront is established as detailed as shown in FIG. 10 and its mathematical algorithm in connection with FIG. 3.

The computer-generated maps and model analysis of the endocardium is periodically updated as the catheter head assembly 100 with its sensor array 7 is moved along the cardiac chamber.

The electrogram is synthetically constructed upon the x-ray fluoroscopy image which is pixelized and voxelized so as to allow the mapping of the wavefront characteristics as it is dimensionally, as well as, graphically layered over the heart morphology. The geometrization of the electrical potential and its maps is further detailed by FIGS. 8 and 9.

Figure 10:
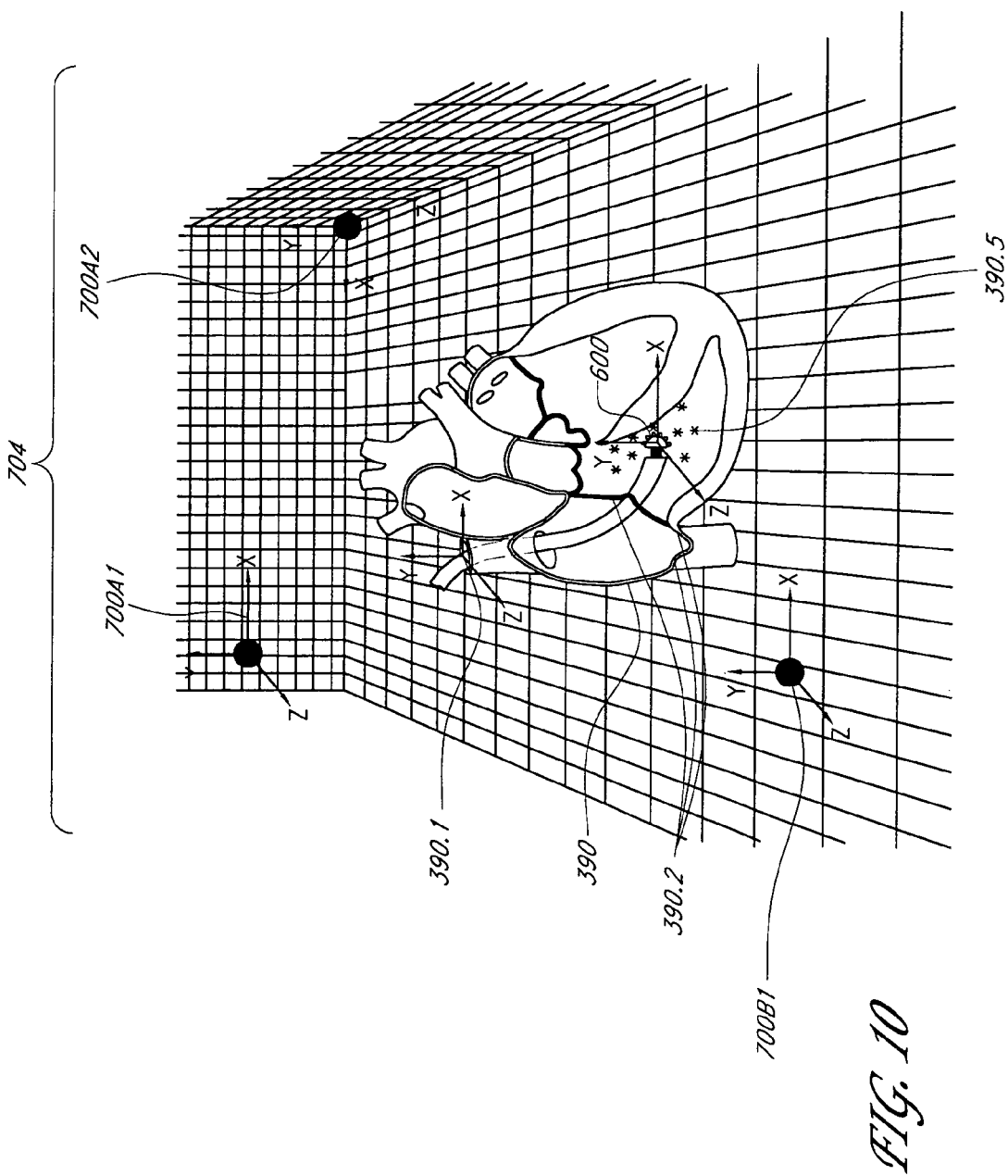
FIG. 10 is an isometric drawing of the image capture and maps formation.

FIG. 10 is an isometric representation of the image capture technique used by the system 1600 in identifying the position and coordinate of the catheter 600 as it moves through the heart chambers. The electric potential measurements taken by the catheter 600 are tracked and gated by the radar 1000 to allow determination of the 3D position coordinates of the catheter tip in real time. The radar and its fiduciary markers provide for the detail dimensional travel map of the catheter as it is sampling (S/H) the electric potential. The system 1600 reconstructs the maps on a grid formed as a 2D pixelized layout superimposed over the reconstructed myocardium chambers or as a voxel 3D vector position. The details of such scheme are outlined by FIGS. 11, 11A, 12, and 12A.

The catheter 600 position is determined by the radar 1000, which maintains a position and orientation above the patient.

In one embodiment, the radar 1000 is set approx. 1 meter from the fiduciary markers placed on or in the patient's body so that phase and range data is defined and beam compensation can be determined. To obtain the calibration points so as to track the moving catheter (range of movements is between 0.2-2 Hz band). The volume integrated, i.e., the cardio chamber (s) is denoted by voxels. Temporal filter such as an FFT denoted by FIG. 11, item 1103, allows the rendering of the signal received from the catheter 600 to be position bound to the original calibrating points.

In one embodiment, the ablation and mapping catheter 600 electromechanical characteristics are; the catheter in closed state 201 is 5.12 mm in diameter. The sensor tip movement is between 1-10 mm diameter (fully opened state 203), the axial movement is 2 mm and the sensor head 100 tool force is 0 to ±35 gram, total radial movement along 360° is 24 position (15° along the circumference), the ablation power is 50 WRF with ablation cut size of 1-2.5 mm. The ablation tool force is 0-35 grams. Eight antennas 8 are spaced along the protective dome 9 which carry eight MOSFET sensors 7.

When the catheter 600 is used while employing the CGCI apparatus, as noted by U.S. patent application Ser. No. 10/690,472, the catheter 600 exerts a force control of 0 to ±37 grams with torque control of 0 to ±35 grams.

The catheter 600 is detected by the radar 1000 and it is placed over the manifold 704 which is placed over the imaging x-ray fluoroscopy 702 while gated by the fiduciary markers 700AX, the normalization procedure performed by the system computer 91 (orthogonal basis) allows the calibration of the catheter tip 2 relative to the fiduciary markers 700AX located on the patient 390 body forming the stereotactic frame used in forming the manifold 704. Navigating the catheter 600 is tracked by denoting the radar initial position as 600× radar (t), the time-varying position of the catheter tip 2, while the fiduciary markers 700AX is denoted by $X_o$ (t) and is determined as voxel o. The other fixed targets are for example the fiduciary markers mounted on the operating table 700BX (fixed targets).

The ranges of the fiduciary markers 700AX and 700BX are denoted by $X_i$ (t); i=1, 2, . . . n. The fiduciary markers are passive devices emitting a radar cross section (RCS) suitable for formation of the manifold 704, while traveling for example through the coronary sinus, the system 1600 record each sign post which facilitates the formation of anatomical sign posts while forming the map (cardio chamber geometry). The sign posts are anatomical in nature and assist in realistic rendering of the synthetically-generated virtual heart surface. Electric potential data sets of ordered pairs <$E_n$, $T_n$> are recorded and are placed on the dimensional grid (manifold 704) generated by the radar 1000. The mapping process is data set of <$E_i$, $T_i$>60, a corresponding <$M_i$, $T_i$>61 and an impedance value <$Z_i$, $T_i$>62, data points are gated to the dimensional grid 704 (the manifold with its fiduciary markers 700AX and permanent reference markers 700BX). The radar 1000 generates a dimensional 3D travel map which is kept for further use. Cardiac motion and pulmonary outputs are gated by the fiduciary marker calibration and body electrogram (ECG). QRS complex cycle is employed in correcting algorithms. The data points <$E_i$, $M_i$, $Z_i$, and $T_i$> are correlated to the grid 704 while correction of position as well as calibration is performed in background mode.

The sensor array 100 with its measuring devices (as detailed by FIGS. 2 and 5) used by the mapping and ablation catheter is designed to enhance the acquisition of temporal/electric potential measurements within the cardiac chambers while correlating space temporal data reconstructed from 3D fields. The system 1600 further provides data sets from and around the ablation area tissue surface. In one embodiment, data of the spread of excitation and the magnitude of the time-varying electric potential in 3D is obtained by the use of the sensors 7, which are galvanically isolated from the tissue to be measured.

The sensor 7 further provides for substantial increase of signal to noise radio due to an device-signal-amplification. The catheter assembly 600 is introduced percutaineously into the heart chambers, by the CGCI apparatus (see U.S. patent application Ser. No. 10/690,472 incorporated herein its entirety).

The catheter tip 2 and the sensor head 100 is initially set at closed position (state 201). The catheter 600 is then activated so as to energize coil 3 and coil 14, deploying the sensor 7 array 100 to its fully open position (state 203).

The sensor array 7 is used to provide readings at two or three positions (201, 202, 203) with incremental radii sensor 7 ($S_1$-$S_8$). The electric potential (with its temporal as well as dimensional elements) is provided to the ECG data interpolation unit 205, based on the data fidelity the system controller 91 instructs the sensor head assembly 100 to move by deploying the magnetic apparatus 50 so as to form measurements along the different states 201, 202, and 203. The axial movement of magnetic assembly 50 with its two electromagnetic coils travels along the guide rail 4.

The axial movement of coils 3 and 14 displaces the arm 6 (which holds the sensors 7 and the RF antenna 8) so as to form an "umbrella" with multiple states (201, 202, and 203). The action of the magnetic assembly 50 is the result of the solenoid action generated by polarity and magnitude of the coils 3 and 14 relative to the permanent magnet 2.

In one embodiment, the CGCI apparatus 1500 is used to generate a magnetic field parallel to the axis of the catheter 600 permanent magnet 2, holding the catheter tip in position (desired position) and the CGCI apparatus produces a gradient in this aligned field without changing its holding direction (the precision of fixing the catheter 600 in its location allows repeated measurements.

The catheter 600 and its associated controller as shown in FIG. 2 can be used to measure the activation time ($t_i$) by sampling the location (site) repeatedly, generating multiple elements of ($E_i$-$T_i$) pairs to characterize the geometrical layout of electric potential on 2D (pixels) or 3D (voxels) maps. Such maps are generated using the electric heart vector (EHV), the correlated magnetic dipole (MHV) as well as impedance values (Z) and superimposition of such maps over the synthetically generated endocardium.

In one embodiment, the endocardium chamber geometry is modeled by an algorithm such as a simplified FEA, which models the wavefront Poynting Energy Vector 49, hence identifying sites of ectopic activation. Automatic activation geometry is further located by the radar signals forming the grid 704 to locate the path of anisotropy due to transmural fiber rotation, that were reconstructed with spatial resultant of >0.5 mm. The data points received from the catheter 600 with its sensors 7, electronically interact with the cardiac cells and such interactions are collected as measured data. The energy wavefront Poynting Energy Vector (PEV) 49 is used in solving the non-linear parabolic partial differential equation. The transmembranes potential typically behaves similar to a cellular automation. Hence, the use of the Hausdorf Neighborhood theorem is an appropriate description of the electrophysiological avalanche. The maps generated by the algorithm described as the Poynting Energy Vector (PEV) 49 can be rendered as images using color for differentiating regions based on density distribution or a mash technique of geodesic line representing the electric potential (on a grid with time domain) as an elevation above the ground potential (zero), and/or as abnormal low voltage represents scar tissue which might express the underlying arrhythmia.

Figure 11:
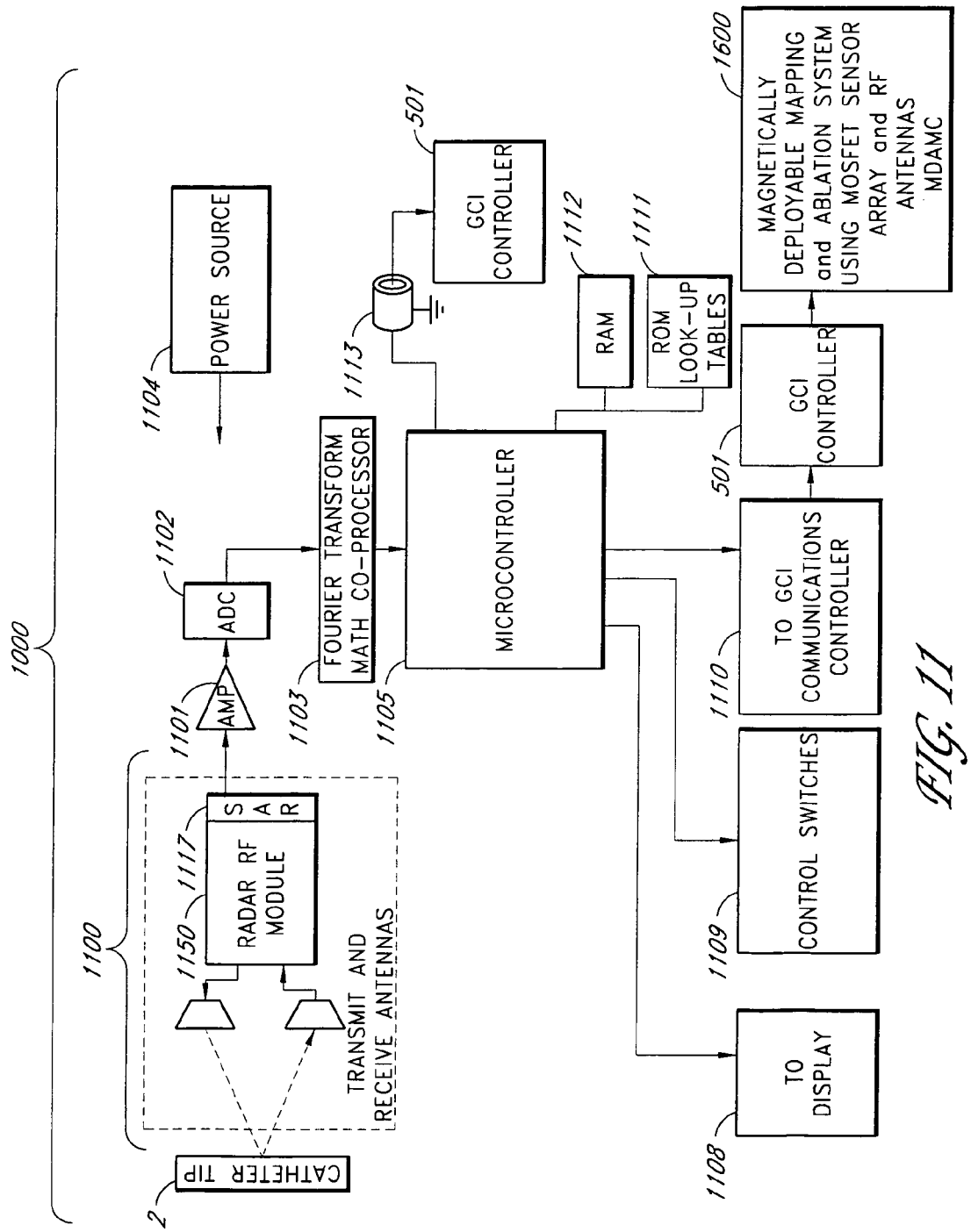
FIG. 11 is a block diagram of the radar used in forming the dimensional manifold of the electrogram.

FIG. 11 is a block diagram of a radar system 1000 used in one embodiment of the CGCI apparatus 1500. The radar 1000 shown in FIG. 11 includes a phased-array radar module 1100 having transmit/receive antenna elements and a Radio Frequency (RF) module 1150. The radar system 1000 includes an amplifier 1101, an A/D converter 1102, a Fast Fourier Transform module 1103, and a microcontroller 1105. The apparatus further includes a memory module in the form of RAM 1112, and a look-up table in the form of a ROM 1111.

One embodiment includes a voice messaging and alarm module 1110, a set of control switches 1109, and a display 1108. The data generated by the radar system 1000 is provided to the GCI apparatus 501 via communications port 1113.

The radar system 1000 includes a phased-array and uses Microwave Imaging via Space-Time (MIST) beam-forming for detecting the catheter tip 2. An antenna, or an array of antennas, is brought relatively near the body of the patient and an ultra wideband (UWB) signal is transmitted sequentially from each antenna. The reflected backscattered signals that are received as radar echoes are passed through a space-time beam-former of the radar unit which is designed to image the energy of the backscattered signal as a function of location. The beam-former focuses spatially on the backscattered signals so as to discriminate from the background clutter and noise while compensating for frequency-dependent propagation effects. The contrast between the dielectric properties of normal tissue and the catheter tip 2 in the regions of interest provides sufficient backscatter energy levels in the image to distinguish normal tissue from the catheter tip 2, affording detection and discern ability. In one embodiment, a data-adaptive algorithm is used in removing artifacts in the received signal due to backscatter from the body tissue interface (e.g., the skin layer). One or more look-up tables containing the known dielectric constants of the catheter tip contrasted against the background dielectric information relative to the biological tissue can be used to identify features in the radar image.

The physical basis for microwave detection of the catheter tip 2 in the biological tissue is based on the contrast in the dielectric properties of body tissue versus the signature of the catheter tip 2. The contrast of the dielectric values of biological tissue versus that of the catheter tip 2 is amplified, filtered and measured.

A typical summary of dielectric properties in living tissues for medical imaging in the range of 10 Hz to 20 GHz and parametric models for the dielectric spectrum of tissues are configured to an ($\in'$) of 5-60 and electrical conductivity ($\sigma$) of 0.065-1.6 Simens/m (S/m) the relative complex permittivity, $\in_r$, of a material is expressed as:

$$\in_r = \in' + j\in''$$

$$\in' = \in/\in_0$$

$$\in'' = \sigma/\in_0 \omega$$

Where $\in$ is the permittivity, $\in_0$ is the permittivity of free space=8.854e-12 Farads/m, $\in''$ is the relative dielectric loss factor, and $\omega$ is the angular frequency.

The return waveform from the radar 1000 is provided to a computer using a software such as MATLAB. A target such as the catheter tip 2 is sampled with a transmitted pulse of approx. 100 ps in duration containing frequency from 400 Hz to 5 GHz with a range of approx. 1 meter in air (the range of the electromagnetic coil location). The radar emits a pulse every 250 ms (4 MHz). The return signals are sampled and integrated together to form the return waveform as measured on circuit 1000. A specific window of data of the radar interaction with the target 2 is obtained and a Fast Fourier Transform (FFT) of the window of data is taken to produce the frequency response of the target 958:

$$X(k) = \sum_{j=1}^{N} x(j) W_N^{(j-1)(k-1)}$$

and by taking a Fast Fourier Transform (FFT) 1103 it is possible to identify the differences between metal 2, or human tissues, etc. The synthetic aperture radar 1117 (SAR) aids in the signal processing by making the antenna seem like it is bigger than it really is, hence, allowing more data to be collected from the area to be imaged.

The radar can use time-domain focusing techniques, wherein the propagation distance is given:

$$d = 2\sqrt{(x)^2 + (z)^2}$$

and alternatively a propagation time computed given by:

$$t = \frac{2\sqrt{(x)^2 + (z)^2}}{v}$$

In one embodiment, target identification and matching is performed by characterizing the target waveform of the catheter tip 2 into a single vector. The dot product is taken from the identification vector and the data whereby, perfectly aligned data and ID results in a dot product of 1, and data perpendicular to the ID (2) is resulting in dot product equal to zero. The radar controller 1105 converts the results to a percent match (dielectric value, conductivity measure) of the data of the identification vector.

The catheter tip 2 has a microwave scattering cross-section that is different relative to biological tissue of comparable size. The difference in scattering cross-section is indicated by the different back-scatter energy registered by the receiver, and processed so as to afford a pictorial representation on a monitor 325 with a contrast between the two mediums. The pictorial view of the catheter tip 2 generated by the radar system 1000 can be superimposed over the X-ray fluoroscopy image 702 and its coordinate data set linked to the GCI controller 501 for use as a position coordinate by the servo feedback loop. In one embodiment, microwave imaging via space-time (MIST) beam-forming is used for detecting back-scattered energy from the catheter tip 2 while the background is biological tissue.

In one embodiment, a data set $<E_t, T_t>$ and $<x; y; z>$ position coordinates are used with the ablation and mapping apparatus 1600 in forming the maps as shown in FIG. 10.

The radar system 1000 detects the presence and location of various microwave scatters, such as the catheter tip 2, embedded in biological tissue 390. The space-time beam-former assumes that each antenna in an array transmits a low-power ultra-wideband (UWB) signal into the biological tissue. The UWB signal can be generated physically as a time-domain impulse 960 or synthetically 1117 by using a swept frequency input. In one embodiment, the radar system 1000 uses a beam-former that focuses the backscattered signals of the catheter tip 2 so as to discriminate against clutter used by the heterogeneity of normal tissue and noise while compensating for frequency-dependent propagation effects. The space-time beam-former achieves this spatial focus by time-shifting the received signals to align the returns from the targeted location. One embodiment of the phased-array radar 1000 forms a band of finite-impulse response (FIR) filters such as high dielectric doping in the antenna cavity, forming the reference signal, where the doping is relative to the device of interest (e.g., catheter tip 2). The signals from the antenna channels are summed to produce the beam-former output. A technique such as weights in the FIR filters can be used with a "least-squares fitting" technique, such as Savitzky-Golay Smoothing Filter to provide enhancement of the received signal and to compute its energy as a function of the dielectric properties versus the scattered background noise of body tissue, thereby providing a synthetic representation of such a signal. The system can distinguish differences in energy reflected by biological tissues 390 and the catheter tip 2 and display such energy differences as a function of location and co-ordinates relative to the fiduciary markers 700Ax through 700Bx. In one embodiment, the radar module 1000 uses an FFT algorithm 1103 which uses a filtering technique to allow the radar 1000 sensor to discern varieties of dielectric properties of specific objects known to be used in a medical procedure, such as a guidewire 379 and/or a catheter 310 with piezoelectric ring 311 and 312 so as to afford differentiation of various types of instruments like catheters, guide-wires, electrodes, etc.

Figure 11B:
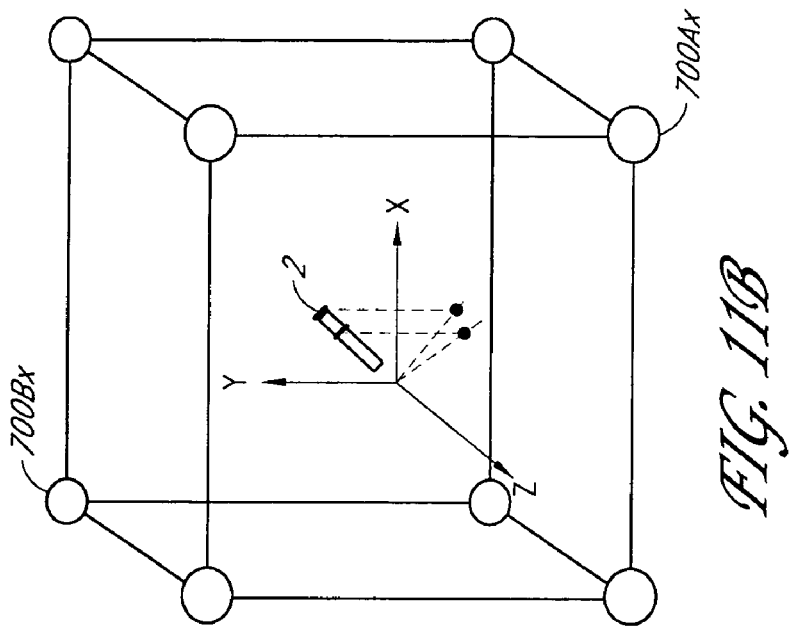
FIGS. 11A and 11B illustrate identification of the catheter position and the anatomical features.
Figure 11A:
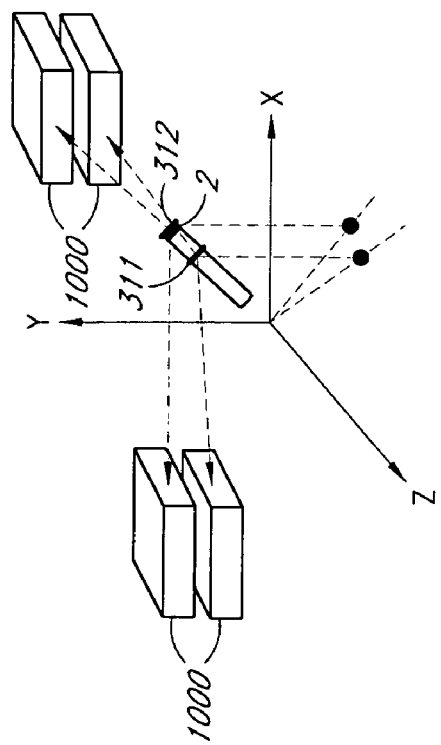

FIG. 11A is a graphical representation of the catheter tip 2 embedded with one, two or more piezoelectric rings 311 and 312 such as Lead-Zirconate-Titanate (PZT) and/or molecularly conjugated polymers such as switchable diodes (polyacetylene). The second harmonics generated by the rings 311 and 312 provide an identifiable return signature in the second harmonic due to the non-linearity of the material. While the fundamental harmonic (e.g., 5 MHz) is transmitted by the radar, the second harmonic (e.g., 10 MHz) is readily distinguishable by the radar system 1000. This allows the radar system 1000 to discern between the catheter tip 2 (which typically has a ferrite such as samarium-cobalt SmCo5, or neodymium-iron-boron, NdFeB) and the PZT rings 311 and 312. The ability to distinguish between the signal return from catheter tip 2 and the PZT rings 311 and 312, allows the radar system 1000 to filter out the background clutter received from the body tissue and to recognize the position and orientation of the rings 311 and 312 and the position co-ordinates of the catheter tip 2. The technique of using two different dielectric properties and electrical characteristics of the tip 2 versus the PZT 311 and 312 provides the catheter tip 2 with a radar signature that can be recognized by the radar system 1000.

FIG. 11B further illustrates how the radar system 1000 with its transmit and receive antennas is used to detect the position co-ordinates and orientation of catheter tip 2 relative to its two PZT rings 311 and 312. A geometrical manipulation is employed by the radar system 1000 and its associated FFT filter 1103 by the resident microcontroller 1105. As shown in FIGS. 4D, 4E, 4F; a catheter-like device is provided with a magnetically-responsive tip 2. In one embodiment, the tip 2 includes a permanent magnet. The polarity of the permanent magnet is marked by two PZT rings where the north pole is indicated by a PZT ring 312 and the distal end of the ferrite where the semi-flexible section 310 of the catheter 376 is marked with the additional PZT ring 311, also marking the south pole of the ferrite.

In one embodiment, the ferrite 2 in the catheter tip is used by the ablation and mapping catheter 600 as described by FIG. 4 and its accompanying descriptions.

The radar system 1000 transmits a burst of energy that illuminates the ferrite catheter tip 2. The return signal from the catheter tip 2 is received by the radar and its position is registered by observing the time of flight of the energy, thereby determining the location of the catheter tip 2 as position co-ordinates in a three-dimensional space. By employing the two PZT rings 311 and 312, the radar detector 1000 is also capable of discerning the location of the tip 2 relative to the two PZT rings so as to afford a measurement of PZT ring 312 relative to the second piezoelectric ring 311 with reference to the position co-ordinates of catheter tip 2. The radar detector 1000 can discern the return signal from PZT rings 311 and 312 due to the non-linear characteristic of PZT material that generates a second harmonic relative to the incident wave. By comparing the strength of the fundamental frequency and the second harmonic, the radar system 1000 is able to discern the position and orientation of the two PZT rings relative to the ferrite 2, thereby providing position and orientation of the catheter tip 2.

FIG. 11B illustrates the technique of measuring the position and orientation of the catheter tip 2 by the use of the radar detector 1000 and using the fiduciary markers 700AX and 700BX to form a frame of reference for the catheter dynamics such as movement relative to the frame of reference. As shown in FIGS. 11A and 11B the fiduciary markers 700AX and 700BX form a manifold 701. The locations of the markers 700AX and 700BX are measured by the radar system 1000.

In one embodiment, the markers are electrically passive and can be made from a polymer or PZT material to allow the radar antenna to receive a signal return which is discernable. Criteria such as the conductivity of a substance such as catheter tip 2 relates at least in part to how much the radar signal is attenuated for a given depth (e.g., the higher the conductivity the higher the loss for a constant depth). An average conductivity of 1 S/m at 1 GHz signal would penetrate the human body 390 approximately 1.8 cm.

The dielectric constant of all targets is typically less than 5 (e.g., cotton(1.35), Nylon 5, etc.). The conductivity of metals is relatively large, and relatively small for most dielectrics (with Nylon on the order 1e-3 and that of cotton and rayon being saturated by that of water, blood and tissue). The relative permittivity of the targets will be in the order of 2-3 orders of magnitude lower than that of the surrounding tissue, and the conductivity of the metals will be 6-7 orders of magnitude greater than that of the surrounding tissue.

The dielectric properties as well as the conductivity measure of the target catheter tip 2 and/or its directional markers PZT rings 311 and 312 allow the radar 1000 to discern the target out of the surrounding clutter (body tissue 390) and perform the task of position definition 2 within the referential frame of fiduciary markers 700AX and 700BX.

In one embodiment, the return waveform is recorded for a static (clutter) environment, and then a target is inserted into the environment and once the clutter is subtracted from the return waveform the radar 1000 processes a target response (clutter is a general term referring to anything the radar will interact with that is not a desired target). In one embodiment, the data is processed and defined in terms of a machine language as model for the CGCI controller 501 and is used by the controller to close the servo loop. In one embodiment, the data generated by the radar 1000 is used for mapping and ablation system 1600 and its computer 91 to form the grid/manifold 704 so as to enable the dimensional placement of the $<E_i T_j>$ pairs $<M_i T_j>$ pairs. The data 60 and 61 are then used by the imaging graphic generator 200 to form the vectoral electrocardiograph maps.

FIGS. 12 and 12A show an image displayed on the monitor 325. The cineoangiographic image 702 of an arterial tree is shown with a reconstructed radar signature of the catheter tip 2. The image 702 contains a numerical grid defined and calculated by the radar 1000 and a data set of coordinate or vector representation of catheter position where the Actual Position (AP) is displayed. A similar data set of catheter position 2 is fed to the CGCI controller 501 or to the ablation computer 91 for the purpose of closing the loop of the servo control system of the CGCI apparatus 1500 and for definition of the dimensional grid for ablation. A graphic depiction of the catheter tip 2 is shown in FIG. 12 where the monitor 325 displays the stereotactic frame formed by the fiduciary markers 700AX and 700BX obtained from the radar signature 1000. The catheter tip 2 is shown in the approximate cube formed by the fiduciary markers 700AX and 700BX. The ensemble of position data relative to coordinates, is formed as dynamic manifold 704. The manifold 704 is used for a processing synchronization of the catheter tip position (AP) relative to the stereotactic frame 701. The process of synchronization is gated in the time domain with the aid of an EKG electrocardiogram 502, whereby the controller 501, internal clock is synchronized with the EKG QRS complex so as to provide a Wiggers' diagram. Synchronization allows the CGCI controller 501 to gate the dimensional data and coordinate set of fiduciary markers so as to move in unison with the beating heart. The technique noted by Image Synchronization 701 allows the ablation catheter 600 and its computer 91 to update the electrocardiograph maps on a real time basis hence enabling the system 1600 to form an accurate view of the mapping and ablation and therefore reduce the use of x-radiation.

Synchronization of the image of the catheter tip 2 or guidewire 379, captured by the radar system 1000, is superimposed onto the fiduciary markers which are represented digitally and are linked dynamically with the image 702. This is done so as to create a combined manifold 704, which is superimposed onto the fluoroscopic image 702, and moves in unison with the area of interest relative to the anatomy in question. For example, the beating heart and its cardio-output; the pulmonary expansion and contraction, or spasm of the patient 390, all these are dynamically captured and linked together so as to achieve a substantial motion in unison between the catheter's tip and the body organ in question.

Synchronization 701 of the catheter tip 2 with its referential markers 700AX and 700BX allows for dynamically calibrating the relative position and accurately gating the cineographic image (or ultrasonic) with the beating heart. Further, the CGCI 1500 and the ablation/mapping catheter 1600 can be used to capture the data set-manifold 704 in the time domain of the patient 390 EKG signal. The CGCI controller 501 and/or the ablation system 1600 can display and control the movement of the catheter tip 2 in unison with the beating heart. Synchronization by the use of fiduciary markers 700AX and 700BX captured by the catheter tip 2, using the data set 704, and superimposing it over the cineographic image 702 and gating it based on EKG signal from the patient's body 390, allows the position data to be linked to the controller 501/91 to close the servo loop and to provide the dimensional grid for forming the electrical maps.

The CGCI controller 501/91 can perform the data synchronization without the active use of x-ray imagery since data of catheter position is provided independently by the radar signal 1000.

The invention is not limited only to the examples described above. Other embodiments and variations will be apparent to one of ordinary skill in that art upon reading the above disclosure. Thus, the invention is limited only by the claims.

What is claimed is:

1. A system for mapping endocardial tissue, said system, comprising:
a catheter having a catheter distal end for insertion into a patient;
a plurality of sensors associated with said distal end, wherein said plurality of sensors are configured to obtain measurements of electrical potential of endocardial tissue in contact with said sensors such that current flow in each sensor is proportional to said electrical potential of said endocardial tissue, wherein each of the plurality of sensors comprise:
a housing in contact with said tissue;
a transistor with a first P-N junction between a first gate junction and a source terminal and between said gate junction and a drain terminal, wherein said source terminal and drain terminal are connected to said housing in contact with said endocardial tissue such that said gate junction assumes said potential of said endocardial tissue;
a computer accessible memory that stores said measurements of said electrical potential of said endocardial tissue obtained by said plurality of sensors over a time duration; and
one or more computer processors that correlate said measurements of said electrical potential of said endocardial tissue with a location of said distal end of said catheter to create an endocardial map of said tissue.

2. The system of claim 1, said distal end of said catheter further comprising a magnet.

3. The system of claim 2, further comprising a deployment mechanism proximate to said catheter distal end and configured to increase a separation between a distal end of a first deployable member and a distal end of a second deployable member.

4. The system of claim 2, wherein said deployment mechanism further comprises a coil that is configured to increase said separation between said distal end of said first deployable member and said distal end of said second deployable member when current is provided to said coil.

5. The system of claim 1, wherein said PN junction is further in communication with a second gate.

6. The system of claim 1, wherein P material of said first PN junction is electrically closer to said tissue than N material and said second electrical contact comprises a second PN junction oriented such that N material of said second PN junction is electrically closer to said tissue than P material.

7. The system of claim 1, further comprising a second PN junction, wherein an said first and second PN junctions are configured with opposite polarity.

8. The system of claim 1, further comprising an antenna in communication with at least one of said plurality of sensors.

9. The system of claim 1, wherein said catheter comprises a lumen.

10. The system of claim 1, further comprising an operator interface unit.

11. The system of claim 1, further comprising:
a magnetic field source for generating a magnetic field, said magnetic field source comprising a first coil corresponding to a first magnetic pole and a second coil corresponding to a second magnetic pole, wherein said first magnetic pole is moveable with respect to said second magnetic pole; and
a system controller for controlling said magnetic field source to control a movement of said catheter distal end, said distal end responsive to said magnetic field, said controller configured to control a current in said first coil, a current in said second coil, and a position of said first pole with respect to said second pole.

12. The system of claim 11, said system controller comprises a closed-loop feedback servo system.

13. The system of claim 11, wherein one or more magnetic field sensors are used to measure said magnetic field.

14. The system of claim 11, said distal end comprising one or more magnetic field sensors.

15. The system of claim 11, said distal end comprising one or more magnetic field sensors for providing sensor data to said system controller.

16. The system of claim 11, wherein said servo system comprises a correction factor that compensates for a dynamic position of an organ, thereby offsetting a response of said distal end of said catheter to said magnetic field such that said distal end moves in substantial unison with said organ.

17. The system of claim 16, wherein said correction factor is generated from an auxiliary device that provides correction data concerning said dynamic position of said organ, and wherein when said correction data are combined with measurement data derived from said plurality of sensors to offset a response of said servo system so that said distal end moves substantially in unison with said organ.

18. The system of claim 11, wherein said auxiliary device is at least one of an X-ray device, an ultrasound device, and a radar device.

19. The system of claim 11, wherein said system controller includes a Virtual Tip control device to allow user control inputs.

20. The system of claim 11, wherein said first magnetic pole is extended and retracted by a hydraulic piston.

21. The system of claim 11, further comprising:
first controller to control said first coil; and
a second controller to control said second coil.

22. The system of claim 21, wherein said first controller receives feedback from a magnetic field sensor.

23. The system of claim 22, wherein said magnetic field sensor comprises a Hall effect sensor.

24. The system of claim 11, wherein said system controller coordinates flow of current through said first and second coils according to inputs from a Virtual tip.

25. The system of claim 24, wherein said Virtual Tip provides tactile feedback to an operator.

26. The system of claim 24, wherein said Virtual Tip provides tactile feedback to an operator according to a position error between an actual position of said distal end and a desired position of said distal end.

27. The system of claim 24, wherein said system controller causes said distal end to follow movements of said Virtual Tip.

28. The system of claim 24, further comprising:
an operator control to allow a user to control force or torque applied to the catheter distal end.

29. The system of claim 11, further comprising:
a controllable magnetic field source having a first cluster of poles and a second cluster of poles;
wherein at least one pole in said first cluster of poles is extendable;
a radar system configured to produce a radar image of organs of said body; and
one or more magnetic sensors to sense a magnetic field.

30. The system of claim 29, said distal end comprising one or more magnetic field sensors.

31. The system of claim 29, said distal end comprising one or more magnetic field sensors for providing sensor data to a system controller.

32. The system of claim 29, further comprising an operator interface unit.

33. The system of claim 29, wherein said first cluster of poles is coupled to said second cluster of poles by a magnetic material.

* * * * *

UNITED STATES PATENT AND TRADEMARK OFFICE
CERTIFICATE OF CORRECTION

| | | |
|---|---|---|
| PATENT NO. | : 7,869,854 B2 | Page 1 of 1 |
| APPLICATION NO. | : 11/362542 | |
| DATED | : January 11, 2011 | |
| INVENTOR(S) | : Shachar et al. | |

It is certified that error appears in the above-identified patent and that said Letters Patent is hereby corrected as shown below:

On page 1 (item 56), in column 2, line 6, under Other Publications, change "Mappaing" to --Mapping--.

In column 2, lines 15-16, please change "percutaineously" to --percutaneously--.

In column 3, line 61, please change "tip" to --Tip--.

In column 9, line 27, please change "anistrophy" to --anisotropy--.

In column 12, line 4, please change "Hadamord" to --Hadamard--.

In column 12, line 40, please change "electrocardigraphic" to --electrocardiographic--.

In column 18, line 25, please change "percutaineously" to --percutaneously--.

In column 26, line 2, please change "cineoangiographic" to --cineangiographic--.

In column 26, lines 48-49, please change "cineographic" to --cinegraphic--.

In column 27, line 43, Claim 5, please change "said said" to --said--.

In column 28, line 26, Claim 18, please change "claim 11," to --claim 17,--.

In column 28, line 44, Claim 24, please change "tip" to --Tip--.

Signed and Sealed this
Twenty-second Day of May, 2012

David J. Kappos
*Director of the United States Patent and Trademark Office*